United States Patent [19]
Yoshida et al.

[11] Patent Number: 5,760,040
[45] Date of Patent: Jun. 2, 1998

[54] INDOLE DERIVATIVE FOR TREATING OVERPRODUCTION OF DIHYDROTESTOSTERONE

[75] Inventors: Kiyoshi Yoshida; Tadashi Kurimoto; Mineo Takei; Hiroki Sato, all of Konanmachi, Japan

[73] Assignee: Zeria Pharmaceutical Co., Ltd., Tokyo, Japan

[21] Appl. No.: 714,079

[22] PCT Filed: Mar. 29, 1995

[86] PCT No.: PCT/JP95/00599

§ 371 Date: May 5, 1997

§ 102(e) Date: May 5, 1997

[87] PCT Pub. No.: WO95/26955

PCT Pub. Date: Oct. 12, 1995

[30] Foreign Application Priority Data

Mar. 30, 1994 [JP] Japan .................. 6-082620

[51] Int. Cl.⁶ .................. A61K 31/405; A61K 31/495; C07D 209/12; C07D 403/10
[52] U.S. Cl. .................. 514/253; 514/419; 544/373; 548/493
[58] Field of Search .................. 514/253, 419; 544/373; 548/493

[56] References Cited

FOREIGN PATENT DOCUMENTS

WO91/12246  8/1991  WIPO .
WO93/17007  9/1993  WIPO .
WO94/14769  7/1994  WIPO .

*Primary Examiner*—Johann Richter
*Assistant Examiner*—Jane C. Osweckí
*Attorney, Agent, or Firm*—Oblon, Spivak, McClelland, Maier & Neustadt, P.C.

[57] ABSTRACT

The present invention relates to an indole derivative represented by formula (1) or a salt thereof, and a pharmaceutical containing the derivative or the salt:

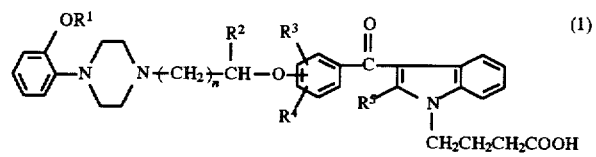

wherein $R^1$ represents lower alkyl; $R^2$ represents hydrogen or phenyl which may be substituted by at least one lower alkyl, lower alkoxy or a halogen atom; $R^3$ represents hydrogen, lower alkyl, lower alkoxy, or phenylalkyloxy which may be substituted by halogen or lower alkyl; $R^4$ represents hydrogen, lower alkyl or lower alkoxy; $R^5$ represents hydrogen or lower alkyl; and n represents an integer of 1 to 5. This compound has the effects of both blocking $\alpha_1$-adrenergic receptors and inhibiting testosterone 5α-reductases, and is useful as a remedy and/or a preventive for diseases caused by dihydrotestosterone overproduction, such as prostatic hypertrophy, and diseases accompanying the same, such as urination disorder, male pattern alopecia, acne, and so forth.

10 Claims, No Drawings

INDOLE DERIVATIVE FOR TREATING OVERPRODUCTION OF DIHYDROTESTOSTERONE

This application is a 371 of PCT/JP95/00599 filed Mar. 29, 1995.

TECHNICAL FIELD

The present invention relates to novel indole derivatives which have testosterone 5α-reductase inhibitory action and thus are effective in the treatment and/or prevention of diseases caused by overproduction of dihydrotestosterone, e.g., prostatic hypertrophy or accompanying urination disorder, male pattern alopecia, and acne; and which have $\alpha_1$-adrenergic receptor blocking action and thus are capable of selectively curing disorders regarding passage through the bladder neck to thereby improve urination disorder.

BACKGROUND ART

Testosterone 5α-reductase is an enzyme that reduces testosterone, a male hormone (androgen), into dihydrotestosterone. The produced dihydrotestosterone has been elucidated to play an important role in the mechanism of the generation and progress of prostatic hypertrophy, male pattern alopecia, and acne (J. Steroid Biochemistry, 11, 609 (1979), J. Clinical Endocrinol and Metabolism, 56, 139 (1983), and Japanese Patent Application Laid-Open (kokai) No. 1-139558). Indoles are known as compounds that exhibit testosterone 5α-reductase inhibitory activities, (Japanese Patent Application Laid-Open (kokai) No. 4-244061, WO93/02050).

α-Adrenergic receptors are known to participate in contraction of smooth muscles. Particularly, recent research has revealed that $\alpha_1$-adrenergic receptors strongly participate in contraction of the sphincter in the human bladder neck (J. Urol., 134, 396 (1985)). Therefore, blockers of the receptors are considered to serve as drugs that are capable of selectively treating urination disorders and frequent urination accompanied by prostatic hypertrophy. As compounds that have a blocking action against such $\alpha_1$-adrenergic receptors, there are known piperazine derivatives (WO89/12634, WO90/03972).

Disurea, which aged people frequently suffer, is caused by constriction of urethra due to the tonus of sympathetic nerves present in the bladder neck or by urinary obstruction associated with prostatic hypertrophy, and makes urination difficult. In recent years, disurea has been treated by the combined use of an $\alpha_1$-adrenergic receptor blocking agent and an antiandrogenic agent. However, this is not satisfactory in view of the drug administration schedule.

Therefore, it is desired to develop drugs having both benefits of symptomatic therapy, which exerts immediate effects as exerted by $\alpha_1$-adrenergic receptors, and of radical therapy, which exhibits its effect slowly but radically, as in the case of testosterone 5α-reductase inhibitors. However, compounds having both $\alpha_1$-adrenergic receptor blocking action and testosterone 5α-reductase inhibitory action have so far not been known.

DISCLOSURE OF THE INVENTION

The present inventors conducted careful studies toward solving the above problems, and surprisingly found that the indole derivatives (1) described below possess strong actions of both blocking $\alpha_1$-adrenergic receptors and inhibiting testosterone 5α-reductases, and thus are useful for the treatment of prostatic hypertrophy and disorders accompanying the same, such as urination disorder, alopecia, and acne. The present invention was accomplished based on this finding.

Accordingly, the present invention provides an indole derivative represented by the following formula (1) or a salt thereof:

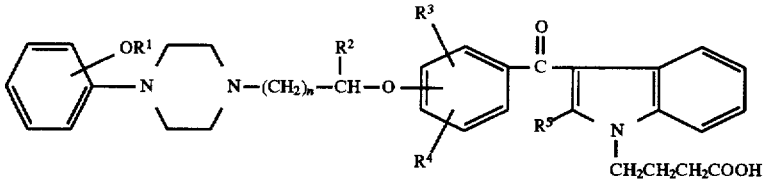

wherein $R^1$ represents lower alkyl; $R^2$ represents hydrogen or phenyl which may be substituted by at least one lower alkyl, lower alkoxy or a halogen atom; $R^3$ represents hydrogen, lower alkyl, lower alkoxy, or phenylalkyloxy which may be substituted by halogen or lower alkyl; $R^4$ represents hydrogen, lower alkyl or lower alkoxy; $R^5$ represents hydrogen or lower alkyl; and n represents an integer of 1 to 5.

The present invention also provides an $\alpha_1$-adrenergic receptor blocker and testosterone 5α-reductase inhibitor comprising as an effective ingredient the indole derivative (1) or a salt thereof.

The present invention also provides a remedy and/or a preventive for prostatic hypertrophy and disorders accompanying the same, such as urination disorder, alopecia, and acne, which comprises as an effective ingredient the indole derivative (1) or a salt thereof.

The present invention further provides a medicine comprising the indole derivative (1) or a salt thereof as well as a carrier for medicines.

The present invention further provides use of the indole derivative (1) or a salt thereof as a medicine.

The present invention still further provides a method for the prevention or treatment of prostatic hypertrophy and disorders accompanying the same, such as urination disorder, alopecia, and acne, characterized by administering an effective amount of the indole derivative (1) or a salt thereof.

BEST MODE FOR CARRYING OUT THE INVENTION

In the present invention, the term "lower" refers to a C1–C6 linear or branched carbon chain, unless otherwise provided.

Accordingly, "lower alkyl groups" include, but are not limited to, methyl, ethyl, n-propyl, isopropyl, n-butyl, isobutyl, s-butyl, t-butyl, n-pentyl, Isopentyl, neopentyl, t-pentyl, 1-methylbutyl, 2-methylbutyl, 1-ethylpropyl, 1,2-dimethylpropyl, and hexyl.

Also, "lower alkoxy groups" include, but are not limited to, methoxy, ethoxy, n-propoxy, isopropoxy, n-butoxy, isobutoxy, s-butoxy, t-butoxy, n-pentyloxy, isopentyloxy, neopentyloxy, t-pentyloxy, 1-methylbutoxy, 2-methylbutoxy, 1-ethylpropoxy, 1,2-dimethylpropoxy, and hexyloxy.

"Halogen atoms" include fluorine, chlorine, bromine, and iodine.

In formula (1), lower alkyl groups represented by $R^1$, $R^3$, $R^4$, and $R^5$ are C1–C6 linear or branched alkyl groups, of which C1–C4 linear or branched alkyl groups are preferred. Particularly, methyl, ethyl, n-propyl, isopropyl, and n-butyl are preferred. Examples of preferred phenyl groups represented by $R^2$ which may be substituted by at least one lower alkyl, lower alkoxy, or a halogen atom include phenyl, C1–C4 alkyl-substituted phenyl, C1–C4 alkoxy-substituted phenyl, and halogen-substituted phenyl. Particularly preferred are phenyl, methylphenyl, ethylphenyl, n-propylphenyl, isopropylphenyl, isobutylphenyl, methoxyphenyl, ethoxyphenyl, chlorophenyl, bromophenyl, and fluorophenyl. Lower alkoxy groups represented by $R^3$ or $R^4$ are C1–C6 linear or branched alkoxy groups, of which C1–C4 linear or branched alkoxy groups are preferred. Particularly, methoxy, ethoxy, n-propoxy, isopropoxy, and n-butoxy are preferred. Examples of phenylalkyloxy groups represented by $R^3$, which may be substituted by halogen or lower alkyl, include phenyl C1–C6 alkyloxy in which the benzene nucleus may be substituted by a halogen atom or a C1–C6 alkyl group, with phenyl C1–C4 alkyloxy in which the benzene nucleus may be substituted by a halogen atom or a C1–C4 alkyl group being more preferred. Examples of particularly preferred $R^3$ groups include benzyloxy, chlorobenzyloxy, fluorobenzyloxy, bromobenzyloxy, methylbenzyloxy, ethylbenzyloxy, isopropylbenzyloxy, n-butylbenzyloxy, phenetyloxy, methylphenetyloxy, phenylpropyloxy, and phenylbutyloxy. n is an integer of from 1 to 5, and particularly preferably from 1 to 3.

The compound (1) of the present invention forms a salt together with an acid or a base. Examples of salts formed together with acids include, but are not limited to, those formed with a variety of acids including mineral acids such as hydrochloric acid, hydrobromic acid, hydroiodic acid, sulfuric acid, nitric acid, and phosphoric acid; organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; and acidic amino acids such as aspartic acid and glutamic acid. Examples of salts formed together with bases include, but are not limited to, those formed with inorganic bases such as sodium, potassium, magnesium, calcium, aluminum, and zinc; those formed with basic amino acids such as lysin and ornithine; and ammonium salts.

The present invention encompasses a variety of solvates of the compound of formula (1), substances of formula (1) having crystalline polymorphism, and R- and S- optical isomers, not to speak of racemic compounds of the formula (1) compounds. Particularly when $R^2$ in formula (1) is phenyl which may have a substituent, the carbon atom to which the $R^2$ is bound becomes an asymmetric carbon atom, thereby providing optical isomerism.

The compound (1) of the present invention may be prepared by a variety of synthesis methods, making use of characteristics on the basis of the backbone structure and kinds of substituents. Typical preparation methods (methods A, B, and C) therefor will be described below. In connection to this, it should be noted that the compounds of the present invention can be prepared via any one of methods A, B, and C, or by any method that is accorded with these methods.

Method A

According to method A, the compound (1) of the present invention is prepared through the following steps (Step A1 to Step A6).

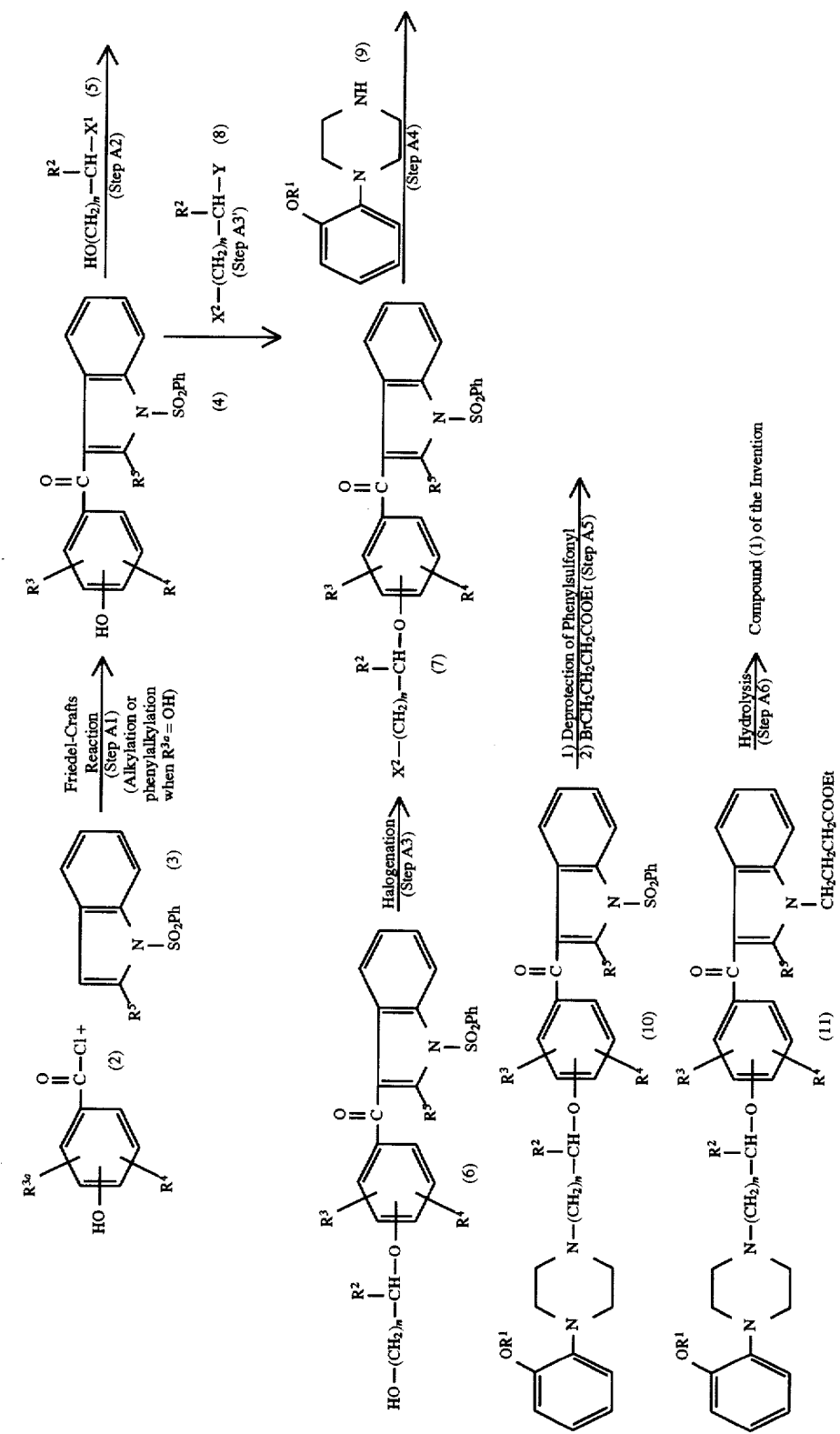

(wherein each of $X^1$ and $X^2$ represents halogen; Y represents halogen or hydroxy; $R^{3a}$ represents hydrogen, hydroxy, lower alkyl, lower alkoxy, or phenylalkyloxy which may be substituted by halogen or lower alkyl; and $R^1$, $R^2$, $R^3$, $R^4$, $R^5$ and n have the same meanings as defined above).

Respective steps will next be described.

Step A1:

Compound (4) can be prepared via a Friedel-Crafts reaction of acid chloride derivative (2) and N-phenylsulfonylindole (3). Under normal circumstances, the reaction is preferably performed in a solvent which does not affect the reaction in the presence of a Lewis acid. As a Lewis acid, tin tetrahalides such as tin tetrachloride and tin tetrabromide; aluminum halides such as aluminum chloride and aluminum bromide; and boron trihalides such as boron trichloride and boron trifluoride are preferred. Examples of solvents include alkylene halides such as methylene chloride and ethylene chloride; and carbon disulfide. The reaction temperature is not particularly limited, and thus the reaction may be performed while cooling, at room temperature, or with heat.

When compound (2) is used in which $R^{3a}$ is hydroxy, compound (4) can be obtained by performing o-alkylation or o-phenylalkylation after completion of a Friedel-Crafts reaction. This may be performed through a reaction using alkyl halide or phenyl alkyl halide; a reaction using an ester of alkyl sulfonic acid or alkyl sulfuric acid; or a reaction using a diazo compound.

Step A2:

Benzoyl indole derivative (6) can be prepared by reacting compound (4) with halohydrin derivative (5). The reaction is preferably performed in a solvent which does not affect the reaction, such as acetone, N,N-dimethylformamide, or methylene chloride, in the presence of a base such as an alkali metal carbonate, e.g., potassium carbonate or sodium carbonate; trialkylamine, e.g., triethylamine or diisopropyletylamine; or a pyridine such as pyridine, lutidine, or 4-dimethylaminopyridine. The reaction is generally performed at room temperature or with heat.

Step A3:

Halide (7) can be prepared by the hydrogenation of the benzoyl indole derivative (6). The hydrogenation reaction may be performed by causing a reaction with a carbon tetrahalide such as carbon tetrabromide or carbon tetrachloride and triphenylphosphine in a solvent such as methylene chloride or acetonitrile. Alternatively, hydrogenation may be performed using phosphorus tribromide, thionyl chloride, etc. The reaction temperature is not particularly limited, and the reaction may be performed while cooling, at room temperature, or with heat.

Step A3':

Halide (7) may also be prepared by reacting compound (4) with compound (8). When Y in compound (8) is hydroxy, the reaction may be performed in a solvent such as ether or tetrahydrofuran in the presence of triphenylphosphine and diethylazodicarboxylate (DEAD). The reaction temperature is not particularly limited, and thus the reaction may be performed while cooling, at room temperature, or with heat.

When an optically active compound (8) is used in the above reaction, the reaction proceeds without causing racemation. Therefore, in the case in which an optically active compound among the compounds of formula (1) of the present invention is to be prepared, it is preferred that an optically active compound (8) be used in this reaction.

When Y in compound (8) is a halogen atom, halide (7) can be prepared in a manner similar to that described in Step A2. Y is preferably a halogen atom that is more reactive than $X^2$.

Step A4:

Compound (10) can be prepared via condensation of halide (7) using a phenyl piperazine derivative (9). The reaction may be performed under conditions similar to those described in Step A2. When halide (7) is a chloromodification, potassium iodide is preferably added to the reaction.

Step A5:

Ester (11) can be prepared by heating compound (10) in methanol or ethanol in the presence of a base such as sodium hydroxide, potassium hydroxide, sodium carbonate, or potassium carbonate, to thereby eliminate the protective phenylsulfonyl group, and subsequently by performing a reaction with ethyl 4-bromobutyrate. The reaction conditions are similar to those employed in Step A2.

Step A6:

The compound (1) of the present invention can be prepared through hydrolysis of the ester (11). The reaction is usually performed in methanol, ethanol, tetrahydrofuran, or a solvent mixture containing any one of these organic solvents and water, in the presence of a base such as an alkali metal hydroxide, e.g., sodium hydroxide or potassium hydroxide; or an alkali metal carbonate, e.g., sodium carbonate or potassium carbonate, at room temperature, while applying mild heat, or with heat.

Method B

According to method B, the compound (1) of the present invention is prepared through the following steps (Step B1 to Step B4) using, as a starting compound, compound (12) which is described in WO93/02050.

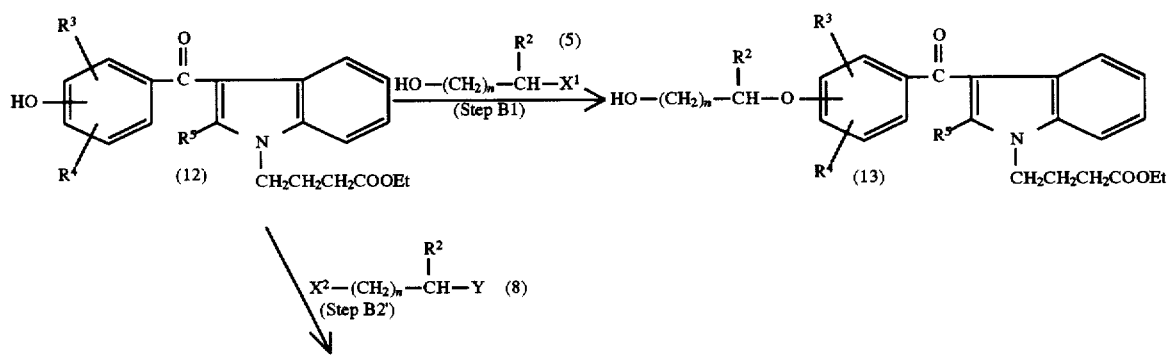

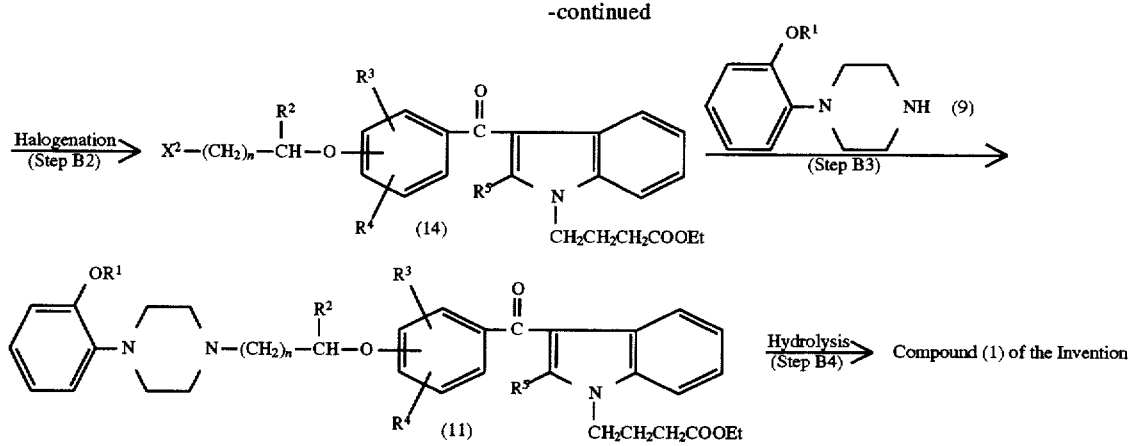

(wherein Y represents halogen or hydroxy; and $R^1$, $R^2$, $R^3$, $R^4$, $R^5$, $X^1$, $X^2$ and n have the same meanings as defined above).

Steps B1, B2, B2', B3, and B4 are performed in manners similar to steps A2, A3, A3', A4, and A6, respectively.

Method C

According to method C, the compound of the present invention is prepared through the following steps (Step C1 to Step C4).

(wherein $X^2$, $R^1$, $R^2$, $R^3$, $R^{3a}$, $R^4$, $R^5$ and n have the same meanings as defined above).

Steps C1, C2, C3, and C4 are performed in manners similar to steps A1, A4, A5 and A6, respectively.

In any case of method A, B, or C, the last hydrolysis step is generally performed in the presence of a base. Therefore, the compound (1) of the present invention can be separated as a salt of the base that is used To convert this into a free carboxylic acid, neutralization using an acid is performed. Transformation into other salts is performed by conventional methods.

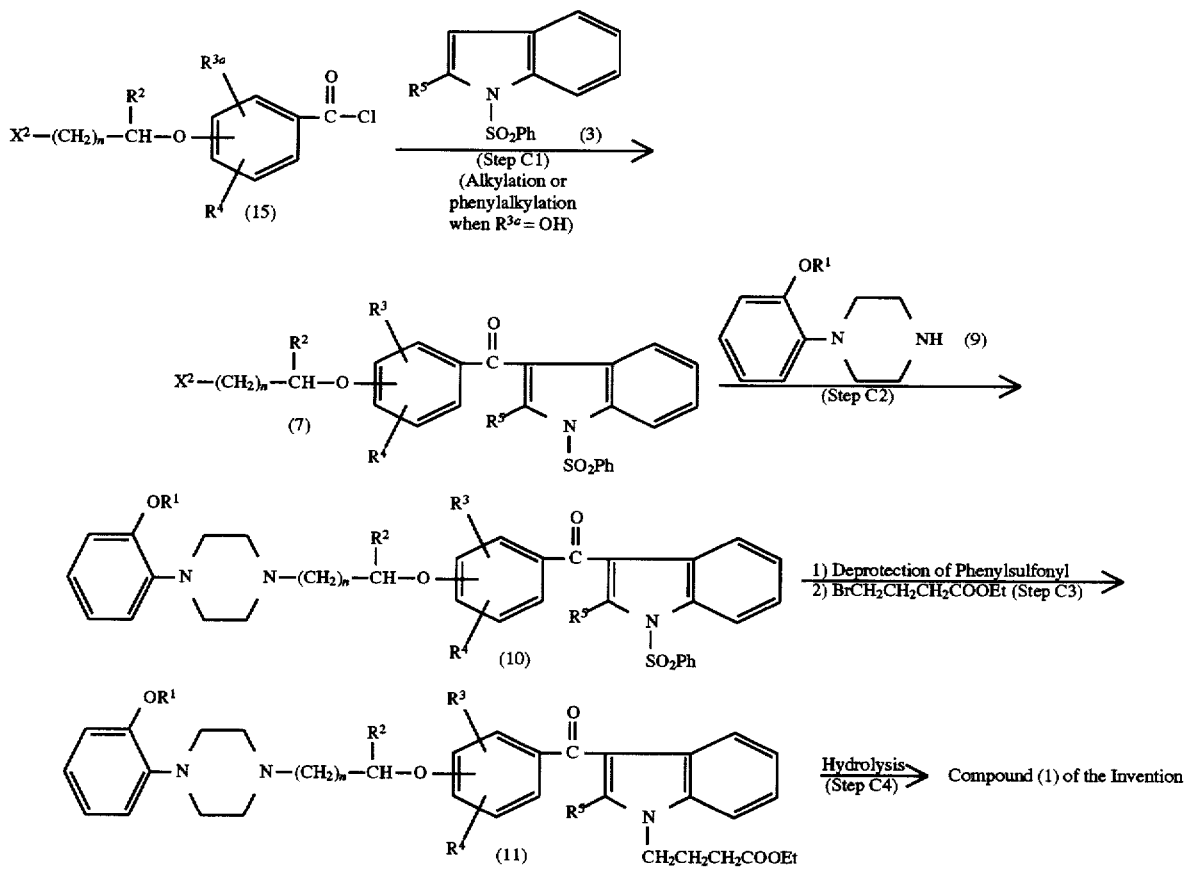

The thus-obtained compound (1) of the present invention exhibits excellent $\alpha_1$-adrenergic receptor blocking action and testosterone 5α-reductase inhibitory action, and is very safe as described below. Therefore, the compound is useful as a preventive or a remedy for prostatic hypertrophy and disorders accompanying the same, such as urination disorder, male pattern alopecia, and acne.

The compound (1) of the present invention, together with pharmaceutically accepted carriers and auxiliaries, may be formulated into preparations for oral or parenteral administration. When preparations for oral administration are formed, the present compound is suitably combined with vehicles such as lactose, mannitol, cornstarch, or crystalline cellulose; binders such as cellulose derivatives, gum arabic, and gelatin; disintegrants such as carboxymethylcellulose•Ca; and lubricants such as talc and magnesium stearate, and is formed into tablets, powders, granules, capsules, etc. These solid preparations may be formed into enteric preparations using a coating base such as hydroxypropylmethylcellulose phthalate, hydroxypropylmethylcellulose acetate succinate, cellulose acetate phthalate, or a methacrylate copolymer. Regarding preparations for parenteral administration, when the compound is combined with water, ethanol, glycerol, or customary surfactants, there may be prepared injection liquids; or when a suppository base is combined, suppositories are prepared.

The dosage may vary depending on age, body weight, symptom of the disease, goal of the treatment, manner of administration, period of administration, etc. Generally, in the case of oral administration, the compound is administered in amounts of 1–2000 mg/day, preferably 10–300 mg/day, as divided in 1 to 3 times a day.

EXAMPLES

The present invention will next be described by way of examples, which should not be construed as limiting the invention. MS data was obtained by fast atom bombardment mass spectroscopy (FABMS) unless otherwise specified.

Example 1

(Method A)

Potassium 4-{3-{3-methoxy-4-{1-(4-methylphenyl)-3-[4-(2-methoxyphenyl)piperazin-1-yl]propoxy}benzoyl}indol-1-yl} butanoate Step 1:

4-Hydroxy-3-methoxybenzoyl chloride, which was prepared from 4-hydroxy-3-methoxybenzoic acid (1.01 g) and thionyl chloride (0.53 ml), was dissolved in dichloroethane (10 ml). The resultant solution was added on ice to a suspension of aluminum chloride (2.08 g) in dichloroethane (20 ml). Following, 1-(phenylsulfonyl)indole (1.85 g) in dichloroethane (10 ml) was added to the resultant with cooling on ice bath and stirred for 1.5 hours at room temperature. The reaction mixture was poured into 1N HCl (100 ml). The precipitate was collected by filtration and washed with water and methanol, obtaining 1.22 g of 3-(4-hydroxy-3-methoxybenzoyl)-1-(phenylsulfonyl)-indole as colorless crystals.

mp: 215°–217° C. (decomposed); MS(m/z):408(MH$^+$); IR(KBr)cm$^{-1}$:3250, 1622, 1582NMR(DMSO-d$_6$)δ:3.87(s, 3H), 6.99(d, 1H) 7.36~7.50(m, 4H), 7.58~7.67(m, 2H) 7.72~7.78(m, 1H), 7.99~8.20(m, 4H) 8.29(s, 1H), 10.06(s, 1H)

Step 2:

1-(4-Methylphenyl)-1,3-propanediol (1.00 g) was dissolved in methylene chloride (30 ml), and 47% hydrobromic acid (3 ml) was added to the resultant solution. After stirring the mixture for 1 hour at room temperature, water was added to separate an organic layer. The organic layer was sequentially washed with saturated sodium bicarbonate solution and brine in this order and dried to remove the solvent. The residue was dissolved in acetone (15 ml). To the solution were added 3-(4-hydroxy-3-methoxybenzoyl)-1-(phenylsulfonyl)indole (1.08 g) obtained in Step 1 and potassium carbonate (1.65 g). The mixture was refluxed for 2 hours. After cooling, the reaction mixture was filtered, and then the solvent was distilled off. The residue was purified by silica gel column chromatography (n-hexane:ethyl acetate=3:1), obtaining 1.04 g of 3-{3-methoxy-4-[1-(4-methylphenyl)-3-hydroxypropoxy]benzoyl}-1-(phenylsulfonyl)indole as a yellow oily substance.

MS (m/z): 556(MH$^+$); IR (KBr) cm$^{-1}$:3600~3250, 1636, 1593, 1578; NMR (CDCl$_3$)δ:2.10~2.40(m, 6 H) 3.80~3.98 (m, 5H), 5.40(dd, 1H) 6.74(d, 1H), 7.13~7.60(m, 11H) 7.86~8.03(m, 4H), 8.18~8.23(m, 1H)

Step 3:

3-{3-Methoxy-4-[1-(4-methylphenyl)-3-hydroxypropoxy] benzoyl}-1-(phenylsulfonyl)indole (0.99 g) obtained in Step 2 was dissolved in methylene chloride (10 ml). Triphenylphosphine (0.71 g) and carbon tetrabromide (1.01 g) were added to the resultant solution while cooling on ice bath and stirred for 30 minutes at room temperature. Saturated sodium bicarbonate solution was added to the reaction mixture to separate an organic layer. The organic layer was washed with brine and then dried. The solvent was distilled off. The residue was purified by silica gel column chromatography (n-hexane:ethyl acetate=9:1), obtaining 0.65 g of 3{(3-methoxy-4-[3-bromo-1-(4-methylphenyl)propoxy]benzoyl}-1-(phenylsulfonyl )indole as a light brown oily substance.

MS (m/z) : 618 (MH$^+$); IR (KBr) cm$^{-1}$:1636, 1593, 1578; NMR (CDCl$_3$)δ:2.27~2.76 (m, 5H) 3.47~3.79(m, 2H), 3.96 (s, 3H) 5.46 (dd, 1H), 6.83 (d, 1H) 7.16~7.61(m, 11H), 7.87~7.93(m, 2H) 7.96~8.02 (m, 2 H), 8.18~8.23 (m,1H)

Step 4:

3-{3-Methoxy-4-[3-bromo-1-(4-methylphenyl)propoxy benzoyl}-1-(phenylsulfonyl)indole (0.59 g) obtained in Step 3 was dissolved in N,N-dimethylformamide (6 ml). 1-(2-Methoxyphenyl)piperazine (0.22 g) and potassium carbonate (0.20 g) were added to the resultant solution and stirred for 3 hours at 60° C. After cooling, water was added to the reaction mixture, followed by extraction with ethyl acetate. The extract was washed with brine and then dried. The solvent was distilled off. The residue was purified by silica gel column chromatography (n-hexane:ethyl acetate=3:1), obtaining 0.56 g of 3{-methoxy -4-(1-(4-methylphenyl) -3-[4- (2-methoxyphenyl )piperazin-1-yl]propoxy}benzoyl}-1-(phenylsulfonyl)indole as a light yellow oily substance.

MS (m/z):730(MH$^+$); IR (KBr) cm$^{-1}$:1636, 1593, 1578; NMR (CDCl$_3$)δ:2.04~2.47(m, 5H) 2.61(t, 2H), 2.63~2.73 (br, 4H) 3.07~3.16(br, 4H), 3.36(s, 3H) 3.96(s, 3H), 5.39(dd, 1H) 6.84~7.03(m, 5H), 7.14~7.59(m, 11H) 7.85~7.92(m, 2H), 7.96~8.01(m, 2H) 8.18~8.2 2(m, 1H)

Step 5:

3-{3-Methoxy-4-{1-(4-methylphenyl)-3-[4-(2-methoxyphenyl)piperazin-1-yl]propoxy}benzoyl}-1-(phenylsulfonyl)indole (0.49 g) obtained in Step 4 was dissolved in methanol (10 ml). Potassium hydroxide (0.60 g) was added to the resultant solution and refluxed for 1 hour. After cooling, the solvent was distilled off. Water was added to the residue, followed by extraction with methylene chloride. The extract was washed with brine and then dried. The solvent was distilled off, obtaining 0.37 g of 3-{3-methoxy- 4-{1-(4-methylphenyl)-3-[4-(2-methoxyphenyl) piperazin-1-yl]propoxy}benzoyl}indole as a light yellow oily substance.

MS (m/z): 590 (MH$^+$); IR (KBr) cm$^{-}$:1595, 1576; NMR (CDCl$_3$)δ:2.00~2.45(m, 5H) 2.50~2.72(m, 6H) 3.04~3.16(br, 4H) 3.84(s, 3H)3.88(s, 3 H), 5.32(t, 1H) 6.73~7.03(m, 5H)7.10~7.44(m, 9H) 7.57(s, 1H),8.30~3.38(m, 1H)

Thus-obtained 3-{3-methoxy-4-{1-( 4-methylphenyl)-3-[4-(2-methoxyphenyl)piperazin-1-yl]propoxy}benzoyl}indole (0.36 g) was dissolved in N,N-dimethylformamide (5 ml). 4-Bromo ethyl butylate (0.12 g) and potassium carbonate (0.13 g) were added to the resultant solution and stirred overnight at room temperature. Water was added to the reaction mixture, followed by extraction with ethyl acetate. The extract was washed with brine and then dried. The solvent was distilled off. The residue was purified by silica gel column chromatography (n-hexane:ethyl acetate=1:1), obtaining 0.28 g of ethyl 4-{3-{3-methoxy-4-{1-(4-methylphenyl)-3-[4-(2-methoxyphenyl)-piperazin-1-yl]propoxy}benzoyl}indol-1-yl}butanoate as a light yellow oily substance.

MS (m/z): 704 (MH$^+$); IR (KBr) cm$^{-1}$:1730, 1624, 1595; NMR (CDCl$_3$)δ:1.19(t, 3H), 2.05~2.46(m, 9H), 2.56~2.73 (m, 6H), 3.06~3.15(br, 4H), 3.86(m, 3H), 3.95(s, 3H), 4.08(q, 2H), 4.23(t, 2H), 5.35(dd, 1H), 6.77~7.03(m, 5H), 7.13~7.46(m, 9H), 7.55(s 1H), 8.33~8.39(m, 1H)

Step 6:

Ethyl 4-{3-{3-methoxy-4-{1-(4-methylphenyl)-3-[4-(2-methoxyphenyl)piperazin-1-yl]propoxy}benzoyl} indol-1-yl}butanoate (2.00 g) was dissolved in ethanol (20 ml). Potassium hydroxide (0.64 g) was added to the resultant solution and stirred overnight at room temperature. After removing the solvent, the residue was purified using an HP-20 column, obtaining 1.34 g of potassium 4-{3-{3-methoxy-4-{1-(4-methylphenyl)-3-[4-(2-methoxyphenyl) piperazin-1-yl]propoxy}benzoyl}indol-1-yl}butanoate as amorphous powder.

MS (m/z):714(MH$^+$); IR (KBr) cm$^{-1}$:1595, 1573; NMR (DMSO-d$_6$)δ:1.84~2.04(m, 5H), 2.10~2.31(m, 4H), 2.44(t, 2H), 2.45~2.55(br, 4H), 2.92~3.01(br, 4H), 3.76(s, 3H), 3.89(s, 3H), 4.24(t, 2H), 5.46(t, 1H), 6.82~6.96(m, 5H), 7.14~7.38(m, 8H), 7.66(d, 1H), 8.00(s, 1H), 8.19~8.24(m, 1H).

Example 2

(Method B)

4-{3-{4-{1-Phenyl-3-[4-(2-methoxyphenyl)piperazin-1-yl]propoxy}benzoyl}indol-yl}butanoic acid Step 1:

1-Phenyl-1,3-propanediol (6.17 g) was dissolved in toluene (200 ml) and 47% hydrobromic acid (20 ml) was added to the resultant solution. The mixture was stirred for 1.5 hours at room temperature. Water was added to the reaction mixture to separate an organic layer. The organic layer was sequentially washed with saturated sodium bicarbonate solution and brine in this order and then dried. The solvent was distilled off. The residue was dissolved in acetone (150 ml). Ethyl 4-{3-(4-Hydroxybenzoyl)indol-1-yl}butanoate (6.33 g) and potassium carbonate (9.95 g) were added to the resultant solution and refluxed for 20 hours.

After cooling, the reaction mixture was filtered, and then the solvent was distilled off. The residue was purified by silica gel column chromatography (n-hexane:ethyl acetate= 2:1), obtaining 7.38 g of ethyl 4-{(3-[4-(1-phenyl-3-hydroxypropoxy)benzoyl]indol-yl}butanoate as colorless crystals.

mp:114°–1150° C. MS (EI, m/z):485(M$^+$); IR (KBr) cm$^{-1}$:3600~3300, 1728, 1600NMR (CDCl$_3$)δ:1.20(t, 3 H), 1.79(t 1H), 2.0 6~2.36(m 6H), 3.75~3.98(m, 2H), 4.09(q, 2H), 4.23(t, 2H), 5.48(dd, 1H), 6.94(d, 2H), 7.25~7.43(m, 8H), 7.51(s, 1H), 7.72(d, 2H), 8.33~8.38(m, 1H)

Step 2:

Ethyl 4-{3-[4-(1-phenyl-3-hydroxypropoxy) benzoyl] indol-1-yl}butanoate (4.00 g) obtained in Step 1 was dissolved in methylene chloride (40 ml). Triphenylphosphine (3.24 g) and carbon tetrabromide (3.24 g) were added to the resultant solution while cooling on ice bath and stirred for 30 minutes at room temperature. Saturated sodium bicarbonate solution was added to the reaction mixture to separate an organic layer. The organic layer was washed with brine and then dried. The solvent was distilled off. The residue was purified by silica gel column chromatography (n-hexane:ethyl acetate=5:1), obtaining 3.97 g of ethyl 4-{3-[4-(3-bromo-1-phenylpropoxy)benzoyl]indol-1-yl}butanoate as colorless oily substance.

MS (m/z)548(MH$^+$); IR (neat) cm$^{-1}$:1728, 1601NMR (CDCl$_3$)δ:1.20(t, 3H), 2.1(quint, 2H), 2.25~2.67(m, 4H), 3.45~3.73(m, 2H), 4.09(q, 2H), 4.24(t, 2H), 5.47(dd, 1H), 6.95(d, 2H), 7.26~7.43(m, 3H), 7.52(s, 1H), 7.74(d, 2H), 8.33~8.39(m, 1H)

Step 3:

Ethyl 4-{3-[4-(3-bromo-1-phenylpropoxy)benzoyl]indol-1-yl}butanoate (1.97 g) obtained in Step 2 was dissolved in N,N-dimethylformamide (20 ml). 1-(2-Methoxyphenyl) piperazine (0.83 g) and potassium carbonate (0.75 g) were added to the resultant solution and stirred overnight at 60° C. After cooling, water was added to the reaction mixture, followed by extraction with ethyl acetate. The resultant extract was washed with brine and then dried. The solvent was distilled off. The residue was purified by silica gel column chromatography (n-hexane:ethyl acetate=2:1), obtaining 1.95 g of ethyl 4-{3-{4-{1-phenyl-3-[4-(2-methoxyphenyl)piperazin-1-yl]propoxy}benzoyl}indol-1-yl}butanoate as a colorless oily substance.

MS (m/z) 660(MH$^+$); IR (KBr) cm$^{-1}$:1730, 1599; NMR (CDCl$_3$)δ: 1.20(t, 3H), 2.01~2.37(m, 6H), 2.52~2.72(m, 6H), 3.06~3.17(br, 4H), 3.86(s, 3H), 4.09(q, 2H), 4.23(t, 2H), 5.37(dd, 1H), 6.84~7.04(m, 6H), 7.25~7.43(m, 8H), 7.52(s, 1H), 7.74(d, 2H), 8.33~8.39(m, 1H).

Step 4:

Ethyl 4-{3-{4-{1-phenyl-3-[4-(2-methoxyphenyl) piperazin-1-yl]propoxy}benzoyl}indol-1-yl}butanoate (1.89 g) obtained in Step 3 was dissolved in ethanol (20 ml). Potassium hydroxide (0.80 g) was added to the resultant solution and stirred for 3 hours at room temperature. After adding acetic acid (2 ml) to the reaction mixture, the solvent was distilled off. Water was added thereto, followed by extraction with ethyl acetate. The resultant extract was washed with brine and dried. The solvent was distilled off. The residue was purified by silica gel column chromatography (methylene chloride: methanol=40:1), obtaining 1.68 g of 4-{3-{4-{1-phenyl-3-[4-(2-methoxyphenyl)piperazin-1-yl] propoxy}benzoyl}indol-1-yl}butanoic acid as amorphous powder.

MS (m/z):632(MH$^+$); IR (KBr) cm$^{-1}$:3500~3250, 1721, 1597; NMR (CDCl$_3$)δ:2.0 8~2.3 2(m, 4H), 2.50~2.61(m, 2H), 3.00~3.55(m, 10H), 3.84(s, 3H), 4.23(t, 2H), 5.56(t, 1H), 6.85~7.10(m, 6H), 7.22~7.43(m, 8H), 7.52(s 1H), 7.72(d, 2H), 8.34~8.42(m, 1H)

Examples 3 to 27

Compounds of the following Examples 3 to 27 were synthesized from adequate material compounds in accordance with the method of Example 1 or 2.

Example 3

Potassium 4-{3-{4-{3-[4-(2-methoxyphenyl)piperazin-1-yl]propoxy}benzoyl}indol-1-yl}butanoate MS (m/z):594(MH$^+$); IR (KBr) cm$^-$:1731, 1599; NMR (DMSO-d$_6$)δ:1.90~2.10(m, 4H), 2.24(t 2H), 2.40~2.70(br, 6H), 2.93~3.06(br, 4H), 3.78(s, 3H), 4.15(t, 2H), 4.31(t, 2H), 8.85~6.98(m, 4H), 7.08(d, 2H), 7.22~7.35(m, 2H), 7.63(d, 1H), 7.81(d, 2H), 8.01(s, 1H), 8.22~8.27(m, 1H)

Example 4

Potassium 4-{3-{4-{1-(4-methylphenyl)-3-[4-(2-methoxyphenyl)piperazin-1-yl]propoxy}benzoyl}indol-1-yl}butanoate MS (m/z):684(MH$^+$); IR (KBr) cm$^{-1}$:1597; NMR (DMSO-d$_6$)δ:1.84~2.22(m, 6H), 2.27(s, 3H), 2.44(t, 2H), 2.45~2.55(br, 4H), 2.90~3.00(br, 4H), 3.76(s, 3H), 4.24(t, 2H), 5.47(t, 1H), 6.82~6.95(m, 4H), 7.02(d, 2H), 7.16~7.36(m, 6H), 7.65(d, 1H), 7.71(d, 2H), 7.95(s, 1H), 8.18~8.23(m, 1H).

Example 5

4-{3-{4-{1-Phenyl-3-[4-(2-isopropoxyphenyl)piperazin-1-yl]propoxy}benzoyl}indol-1-yl}butanoic acid MS (m/z):660(MH$^+$); IR (KBr) cm$^{-1}$:3650~3300, 1720, 1599; NMR (CDCl$_3$)δ:1.32(s, 3H), 1.34(s, 3H), 2.05~2.42(m, 6H), 2.80~3.02(m, 6H), 3.10~3.28(br, 4H), 4.19(t, 2H), 4.57(sept, 1H), 5.33(dd, 1H), 6.80~7.00(m, 6H), 7.20~7.42(m, 8H), 7.53(s, 1H), 7.71(d, 2H), 8.33~8.39(m, 1H)

Example 6

4-{3-{4-{1-Phenyl-4-[4-(2-methoxyphenyl)piperazin-1-yl]butoxy}benzoyl}indol-1-yl}butanoic acid MS (m/z):646(MH$^+$); IR (KBr) cm$^{-1}$:3500~3300, 1725, 1597; NMR (CDCl$_3$)δ:1.90~2.32(m, 8H), 2.95~3.65(m, 10H), 3.84(s, 3H), 4.23(t, 2H), 5.26(t, 1H), 6.84~7.10(m, 6H), 7.23~7.42(m, 8H), 7.52(s, 1H), 7.72(d, 2H), 8.35~8.41(m, 1H).

Example 7

4-{3-{4-{1-Phenyl-4-[4-(2-isopropoxyphenyl)piperazin-1-yl]butoxy}benzoyl}indol-1-yl}butanoic acid MS (m/z):674(MH$^+$); IR (KBr) cm$^{-1}$:3300, 1722, 1599; NMR (CDCl$_3$)δ:1.34(d, 6H), 1.85~2.30(m, 8H), 2.87~3.03(m, 2H), 3.06~3.25(br, 4H), 3.30~3.44(br, 4H), 4.22(t, 2H), 4.57(sept, 1H), 5.25(t, 1H), 6.82~7.03(m, 6H), 7.22~7.42(m, 8H), 7.53(s, 1H), 7.72(d, 2H), 8.36~8.41(m, 1H)

Example 8

Potassium 4-{3-{4-{1-(4-methylphenyl)-3-[4-(2-isopropoxyphenyl)piperazin-1-yl]propoxy}benzoyl}indol-1-yl}butanoate MS (m/z):712 (MH$^+$); IR (KBr) cm$^{-1}$:1597; NMR (DMSO-d$_6$)δ:1.24(d, 6H), 1.86~2.24(m, 6H), 2.27(s, 3H), 2.44(t, 2H) 2.45~2.55(br, 4H), 2.91~3.01(br, 4H), 4.25(t, 2H), 4.57(sept, 1H), 5.48(t, 1H), 6.84~6.90(m, 4H), 7.01(d, 2H), 7.13~7.37(m, 6H), 7.63(d, 1H), 7.71(d, 2H), 7.96(s, 1H), 8.19~8.24(m 1H).

Example 9

Potassium 4-{3-{4-{1-(4-ethylphenyl)-3-[4-(2-methoxyphenyl)piperazin-1-yl]propoxy}benzoyl}indol-1-yl}butanoate MS (m/z):698(MH$^+$); IR (KBr) cm$^{-1}$:1597; NMR (DMSO-d$_6$)δ:1.16(3H), 1.85~2.25(m, 6H), 2.45(t, 2H), 2.46~2.54(br, 4H), 2.58(q, 2H), 2.90~3.00(br, 4H), 4.24(t, 2H), 5.48(t, 1H), 6.83~6.90(m, 4H), 7.02(d, 2H), 7.16~7.40(m, 6H), 7.64(d, 1H), 7.71(d, 2H), 7.95(s, 1H), 8.18~8.23(m, 1H)

Example 10

Potassium 4-{3-{3-methoxy-4-{1-(4-methylphenyl)-3-[4-(2-ethoxyphenyl)piperazin-1-yl]propoxy}benzoyl}indol-1-yl}butanoate MS (m/z):728(MH$^+$); IR (KBr) cm$^{-1}$:1598; NMR (DMSO-d$_6$)δ:1.33(t, 3H), 1.84~2.25(m, 6H), 2.27(s, 3H), 2.44(t, 2H), 2.45~2.55(br, 4H), 2.95~3.05(br, 4H), 3.89(s, 3H), 3.99(q, 2H), 4.24(t, 2H), 5.45(t 1H), 6.82~6.95(m, 5H), 7.13~7.37(m, 8H), 7.64(d, 1H), 7.99(s, 1H), 8.19~8.24(m, 1H).

Example 11

Potassium 4-{3-{3-methoxy-4-{1-(4-methylphenyl)-3-[4-(2-isopropoxyphenyl)piperazin-1-yl]propoxy}benzoyl}indol-1-yl}butanoate MS (m/z):742(MH$^+$); IR(KBr)cm$^{-1}$:1593, 1578; NMR (DMSO-d$_6$)δ:1.22(s, 3H), 1.25(s, 3H), 1.84~2.03(m, 5H), 2.10~2.30(m, 4H), 2.44(t, 2H), 2.45~2.55(br, 4H), 2.92~3.04(br, 4H), 3.89(s, 3H), 4.24(t, 2H), 4.57(sept, 1H), 5.46(t, 1H), 6.83~6.95(m, 5H), 7.13~7.38(m, 3H), 7.64(d, 1H), 8.00(s, 1H), 8.20~8.24(m 1H).

Example 12

4-{3-{3-methoxy-4-{1-(4-ethylphenyl)-3-[4-(2-methoxyphenyl)piperazin-1-yl]propoxy}benzoyl}indol-1-yl}butanoic acid MS (m/z):690(MH$^+$); IR(KBr)cm$^{-1}$:1718, 1595; NMR (CDCl$_3$)δ:1.18(t, 3H), 2.05~2.50(m, 6H), 2.59(q, 2H), 2.94(t, 2 H), 2.95~3.06(b, 4H), 3.17~3.27(br, 4H), 3.34(s, 3H), 3.91(s, 3H), 4.20(t 2H), 5.33(t, 1H), 6.78~6.91(m, 12H), 6.98~7.05(m, 1H), 7.12(d, 2H), 7.24~7.31(m, 5H), 7.36~7.42(m, 2H), 7.56(s, 1H), 8.35~3.40(m, 1H)

Example 13

Potassium 4-{3-{3-methoxy-4-{1-(4-isobutylphenyl)-3-[4-(2-methoxyphenyl)piperazin-1-yl]propoxy}benzoyl}indol-1-yl}butanoate MS(m/z):756(MH$^+$); IR(KBr)cm$^{-1}$:1598; NMR(DMSO-d$_6$)δ:0.84(d, 6H), 1.72~2.28(m, 7H), 2.35~2.50(m, 2H), 2.42(t, 2H), 2.46~2.56(br, 4H), 2.88~3.00(br, 4H), 3.76(s, 3H), 3.89(s, 3H), 4.25(t, 2H), 5.46(t, 1H), 6.84~6.97(m, 5H), 7.10~7.39(m, 3H), 7.62(d, 1H), 8.00(s, 1H), 8.19~8.25(m, 1H)

Example 14

Potassium 4-{3-{3-methoxy-4-{1-phenyl-3-[4-(2-methoxyphenyl)piperazin-1-yl]propoxy}benzoyl}indol-1-yl}butanoate MS(m/z):700(MH$^+$); IR(KBr)cm$^{-1}$:1593, 1572; NMR (DMSO-d$_6$)δ:1.87~2.27(m, 6H), 2.46(t, 2H), 2.45~2.55(br, 4H), 2.90~3.02(br, 4H), 3.76(s 3H), 3.90(s, 3H), 4.25(t, 2H), 5.51(t, 1H), 6.82~7.00(m, 5H), 7.18~7.50(m, 8H), 7.64(d, 1H), 8.00(s, 1H), 8.20~8.25(m, 1H)

Example 15

Potassium 4-{3-{3-methoxy-4-{1-phenyl-3-[4-(2-ethoxyphenyl)piperazin-1-yl]propoxy}benzoyl}indol-1-yl}butanoate MS(m/z):714(MH⁺); IR(KBr)cm⁻¹:1593, 1572; NMR (DMSO-d₆)δ1.32(t, 3H), 1.82~2.27(m, 6H), 2.46(t, 2H), 2.45~2.55(br, 4H), 2.93~3.04(br, 4H), 3.90(s, 3H), 3.99(q, 2H), 4.25(t 2H), 5.51(t, 1H), 6.80~6.92(m, 4H), 6.95(d, 1H), 7.18~7.49(m, 9H), 7.66(d, 1H), 8.01(s, 1H), 8.20~8.26(m, 1H)

Example 16

Potassium 4-{3-{3-methoxy-4-{1-phenyl-3-[4-(2-isopropoxyphenyl)piperazin-1-yl]propoxy}benzoyl}indol-1-yl}butanoate MS(m/z):728(MH⁺); IR(KBr)cm⁻¹:1728, 1595, 1578; NMR(DMSO-d₆)δ:1.22(s, 3H), 1.25(s, 3H), 1.82~2.26(m, 6H), 2.46(t, 2H), 2.45~2.55(br, 4H), 2.93~3.03(br, 4H), 3.90(s, 3H), 4.24(t, 2H), 5.51(t, 1H), 6.87(s, 4H), 6.94(d, 1H), 7.18~7.47(m, 9H), 7.65(d, 1H), 8.01(s, 1H), 8.20~8.26 (m, 1H)

Example 17

4-{3-{3-Methoxy-4-[1-phenyl-4-[4-(2-methoxyphenyl)-piperazin-1-yl]butoxy}benzoyl}indol-1-yl}butanoic acid MS(m/z):676(MH⁺) IR(KBr)cm⁻¹:3431, 1718, 1595; NMR(CDCl₃)δ:1.91~2.28(m, 8H), 2.94~3.06(br, 2H), 3.10~3.22(br, 4H), 3.30~3.40(br 4H), 3.84(s, 3H), 3.91(s, 3H), 4.21 (t, 2H), 5.27(t, 1H), 6.78(d, 1H), 6.83~6.94(m, 3H), 6.98~7.07(m, 1H), 7.20~7.43(m, 10H), 7.56(s, 1H), 8.35~8.40(m, 1H)

Example 18

Potassium 4-{3-{3-methoxy-4-{1-phenyl-5-[4-(2-methoxyphenyl)piperazin-1-yl]pentyloxy}benzoyl}indol-1-yl}butanoate MS(m/z):728(MH⁺); IR(KBr)cm⁻¹:1593; NMR(DMSO-d₆)δ:1.30~1.58(m, 4H), 1.75~2.10(m, 6H), 2.29(t, 2H), 2.40~2.50(br, 4H), 2.87~2.97(br, 4H), 3.75(s, 3H), 3.89(s, 3H), 4.24(t, 2H), 5.42(t, 1H), 6.83~6.97(m, 5H), 7.17~7.45 (m, 9H), 7.65(d, 1H), 7.99(s, 1H), 8.19~8.24(m, 1H)

Example 19

Potassium 4-{3-{3-methoxy-4-{1-(4-bromophenyl)-3-[4-(2-methoxyphenyl)piperazin-1-yl]propoxy}benzoyl}indol-1-yl}butanoate MS(m/z):778(MH⁺); IR(KBr)cm⁻¹:1595, 1572; NMR (DMSO-d₆)δ:1.83~2.25(m, 6H), 2.45(t, 2H), 2.45~2.55(br, 4H), 2.92~3.00(br, 4H), 3.76(s, 3H), 3.90(s, 3H), 4.25(t, 2H), 5.52(t, 1H), 6.82~6.97(m, 5H), 7.18~7.45(m, 6H), 7.57(d, 2H), 7.67(d, 1H), 8.01(s, 1H), 8.20~8.24(m, 1H)

Example 20

Potassium 4-{3-{4-{1-(4-methoxyphenyl)-3-[4-(2-methoxyphenyl)piperazin-1-yl]propoxy}benzoyl}indol-1-yl}butanoate MS(m/z):700(MH⁺); IR(KBr)cm⁻¹:1597, 1570; NMR (DMSO-d₆)δ:1.85~2.21(m, 6H), 2.42(t, 2H), 2.44~2.54(br, 4H), 2.90~3.01(br, 4H), 3.73(s, 3H), 3.76(s, 3H), 4.24(t, 2H), 5.47(t, 1H), 6.83~6.97(m, 5H), 7.03(d, 2H), 7.18~7.30 (m, 2H), 7.38(d, 2H), 7.66(d, 1H), 7.72(d, 2H), 7.95(s, 1H), 8.19~8.24(m, 1H)

Example 21

4-{3-{3,5-Dimethoxy-4-{1-(4-methylphenyl)-3-[4-(2-methoxyphenyl)piperazin-1-yl]propoxy}benzoyl}indol-1-yl}butanoic acid MS(m/z):706(MH⁺) IR(KBr)cm⁻¹:3600~3200, 1719, 1624, 1578; NMR(DMSO-d6)δ:1.95~2.55(m, 8H), 2.90~3.50(br, 8H), 3.77(s, 3H), 3.80(s, 6H), 4.31(t, 2H), 5.44(t, 1H), 6.83~6.98(m, 4H), 7.02(s, 2H), 7.10~7.35(m, 6H), 7.63(d, 1H), 8.09(s, 1H), 8.18~8.23(m, 1H)

Example 22

4-{3-{2,3-Dimethyl-4-{1-(4-methylphenyl)-3-[4-(2-methoxyphenyl)piperazin-1-yl]propoxy}benzoyl}indol-1-yl}butanoic acid MS(m/z):674(MH⁺); IR(KBr)cm⁻¹:1628, 1590; NMR (CDCl₃)δ:1.38~2.82(m, 15H), 2.45~2.65(br, 6H), 2.93~3.03 (br, 4H), 3.76(s, 3H), 4.21(t, 2H), 5.42(t, 1H), 6.82~6.97(m, 4H), 7.06(d, 1H), 7.14~7.35(m, 7H), 7.57~7.65(m, 2H), 8.19(d, 1H)

Example 23

Potassium 4-{3-{4-{1-(4-methylphenyl)-3-[4-(2-methoxyphenyl)piperazin-1-yl]propoxy}benzoyl}-2-methylindol-1-yl}butanoate MS(m/z):698(MH⁺) IR(KBr)cm⁻¹:1732, 1597; NMR (CDCl₃)δ:1.60~1.80(m, 4H), 1.95~2.05(m, 2H), 2.22(s, 3H), 2.28(s, 3H), 2.51(t, 2H), 2.54~2.64(br, 4H), 3.00~3.10 (br, 4H), 3.65~3.75(br, 2H), 3.82(s, 3H), 5.26(t, 1H), 6.70~7.14(m, 2H), 7.19(d, 1H), 7.55(d, 2H),

Example 24

4-{3-{3-Benzyloxy-4-{3-[4-(2-methoxyphenyl)piperazin-1-yl]propoxy}benzoyl}indol-1-yl}butanoic acid MS(m/z):662(MH⁺); IR(KBr)cm⁻¹:1595, 1561; NMR (DMSO-d₆)δ:1.90~2.15(m, 6H), 2.40~2.60(m, 6H), 2.90~3.00(br, 4H), 3.77(s, 3H), 4.10~4.30(m, 4H), 5.22(s, 2H), 6.85~6.95(m, 4H), 7.14(d, 1H), 7.22~7.51(m, 9H), 7.63~7.66(m, 1H), 7.95(s, 1H), 8.22~8.25(m, 1H), 13.00(br, 1H).

Example 25

Sodium 4-{3-{4-{3-[4-(2-methoxyphenyl)piperazin-1-yl]propoxy}-3-(4-methylphenylmethoxy)benzoyl}indol-1-yl}butanoate MS(m/z):698(MH⁺); IR(KBr)cm⁻¹:1595, 1500; NMR (DMSO-d₆)δ:190~2.18(m, 6H), 2.30(s, 3H), 2.44~2.59(m, 6H), 2.90~3.00(br, 4H), 3.77(s, 3H), 4.10~4.20(m, 2H), 4.23~4.30(m, 2H), 5.16(s, 2H), 6.85~6.95(m, 4H), 7.10~7.45(m, 9H), 7.60~7.66(m, 1H), 7.96(s, 1H), 820~8.25 (m, 1H),

Example 26

4-{3-{3-Benzyloxy-4-{1-(4-methylphenyl)-3-[4-(2-methoxyphenyl)piperazin-1-yl]propoxy}benzoyl}indol-1-yl}butanoic acid MS(m/z):752(MH⁺); IR(KBr)cm⁻¹:1595, 1572; NMR (CDCl₃)δ:2.02~2.41(m, 9H), 2.75~2.90(m, 6H), 3.06~3.18 (br, 4H), 3.83(s, 3H), 4.16(t, 2H), 5.17(s, 2H), 5.24~5.32(m, 2H), 6.80~7.11(m, 7H), 7.20~7.50(m, 13H), 8.36~8.39(m, 1H)

Example 27

4-{3-{3-Methoxy-4-{1-(4-fluorophenyl)-3-[4-(2-methoxyphenyl)piperazin-1-yl]propoxy}benzoyl}indol-1-yl}butanoic acid MS(m/z):680(MH⁺); IR(KBr)cm⁻¹:1595, 1578; NMR (CDCl₃)δ:2.10~2.43(m, 6H), 2.78~2.87(m, 2H), 2.90~3.00

(br, 4H), 3.12~3.21(br, 4H), 3.84(s, 3H), 3.91(s, 3H), 4.24 (m, 3H), 5.32~5.39(m 1H), 6.80~6.91(m, 4H), 6.96~7.05(m, 3H), 7.25~7.43(m, 7H), 7.54(s, 1H), 8.35~8.41(m, 1H)

(br, 4H), 2.85~2.95(br, 4H), 3.74(s, 3H), 4.15~4.30(m, 2H), 5.44(t, 1H), 6.75~6.96(m, 4H), 7.10~7.40(m, 10H), 7.62~7.68(m, 1H), 7.79~7.82(m, 1H), 8.20~8.26(m, 1H)

The structures of the compounds obtained in Examples 1 through 27 are shown in Table 1.

TABLE 1

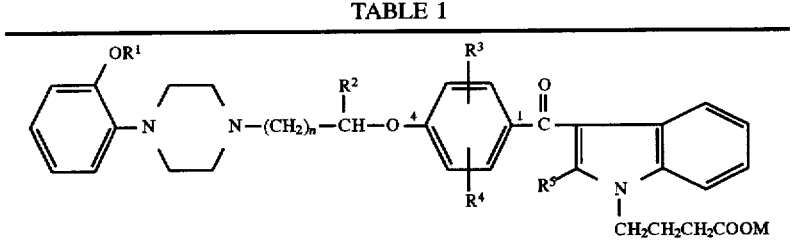

| Example No. | R1 | n | R2 | R3 | R4 | R5 | M |
|---|---|---|---|---|---|---|---|
| 1 | Me | 2 | 4-Me—Ph | 3-MeO | H | H | K |
| 2 | Me | 2 | Ph | H | H | H | H |
| 3 | Me | 2 | H | H | H | H | K |
| 4 | Me | 2 | 4-Me—Ph | H | H | H | K |
| 5 | i-Pr | 2 | Ph | H | H | H | H |
| 6 | Me | 3 | Ph | H | H | H | H |
| 7 | i-Pr | 3 | Ph | H | H | H | H |
| 8 | i-Pr | 2 | 4-Me—Ph | H | H | H | K |
| 9 | Me | 2 | 4-Et—Ph | H | H | H | K |
| 10 | Et | 2 | 4-Me—Ph | 3-MeO | H | H | K |
| 11 | i-Pr | 2 | 4-Me—Ph | 3-MeO | H | H | K |
| 12 | Me | 2 | 4-Et—Ph | 3-MeO | H | H | H |
| 13 | Me | 2 | 4-i-Bu—Ph | 3-MeO | H | H | K |
| 14 | Me | 2 | Ph | 3-Meo | H | H | K |
| 15 | Et | 2 | Ph | 3-MeO | H | H | K |
| 16 | i-Pr | 2 | Ph | 3-Meo | H | H | K |
| 17 | Me | 3 | Ph | 3-MeO | H | H | H |
| 18 | Me | 4 | Ph | 3-MeO | H | H | K |
| 19 | Me | 2 | 4-Br—Ph | 3-MeO | H | H | K |
| 20 | Me | 2 | 4-MeO—Ph | H | H | H | K |
| 21 | Me | 2 | 4-Me—Ph | 3-MeO | 5-MeO | H | H |
| 22 | Me | 2 | 4-Me—Ph | 2-Me | 3-Me | H | H |
| 23 | Me | 2 | 4-Me—Ph | H | H | Me | K |
| 24 | Me | 2 | H | 3-PhCH$_2$O | H | H | H |
| 25 | Me | 2 | H | 3-(4-Me-PhCH$_2$O) | H | H | Na |
| 26 | Me | 2 | 4-Me—Ph | 3-PhCH$_2$O | H | H | H |
| 27 | Me | 2 | 4-F—Ph | 3-MeO | H | H | H |

In the Table, Me stands for methyl, Et stands for ethyl, i-Pr stands for isopropyl, i-Bu stands for isobutyl, Meo stands for methoxy, and Ph stands for phenyl.

Example 28

Similar to the method of Example 2, the following pound was synthesized.

Potassium 4-{3-{3-{1-(4-methylphenyl)-3-[4-(2-methoxyphenyl)piperazin-1-yl]propoxy}benzoyl}indol-1-yl}butanoate

Example 29

Potassium S-4-{3-{4-{1-(4-methylphenyl)-3-[4-(2-methoxyphenyl)piperazin-1-yl]propyloxy}benzoyl}indol-1-yl}butanoate Step 1:
S-5,5-diphenyl-2-methyl-3,4-propano-1,3,2-oxazabololidine (5.54 g) was dissolved in 1.0 M borane-tetrahydrofuran (120 ml) under argon while cooling on ice bath. Subsequently, 4'-methyl-3-chloropropicophenone

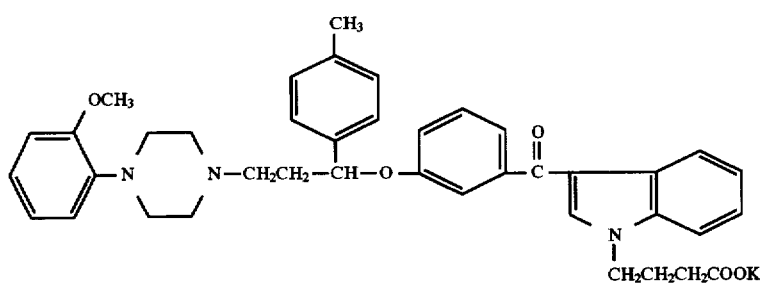

MS(m/z):684(MH$^+$); IR(KBr)cm$^{-1}$:1574; NMR(DMSO-d$_6$)δ:1.86~2.20(m, 6H), 2.27(s, 3H), 2.44(t, 2H), 2.46~2.56

(36.5 g) in tetrahydrofuran (200 ml) was added dropwise over 1 hour and stirred for 30 minutes. 1N HCl (40 ml) was added to the reaction mixture and stirred for a while. Then, the solvent was distilled off. 1N HCl was added to the residue, followed by extraction with ethyl acetate. The extract was sequentially washed with saturated sodium bicarbonate solution and brine in this order and then dried. The solvent was distilled off. The residue was recrystallized with n-hexane (200 ml), obtaining 17.3 g of R-(+)-3-chloro-1-(4-methylphenyl)-1-propanol as colorless crystals.

mp: 48°–50° C.; MS(EI, m/z):184, 186(M$^+$); IR(KBr)cm$^{-1}$:3300; NMR(CDCl$_3$)δ:2.00~2.30(m, 2H), 3.50~3.60(m, 1H), 3.67~3.78(m, 1H), 4.90(quint., 1H), 7.15~7.30(m, 4 H) [α]$_D$+22.0°(c=1, CHCl$_3$)

Step 2:

R-(+)-3-chloro-1-(4-methylphenyl)-1-propanol (16.6 g) obtained in Step 1 and ethyl 4-[3-(4-hydroxybenzoyl)indol-1-yl]butanoate (31.7 g) were dissolved in tetrahydrofuran (350 ml). Triphenylphosphine (28.3 g) and diethylazodicarboxylate (20 ml) were added to the resultant solution while cooling on ice bath and stirred for 3 hours at room temperature. After removing the solvent, the residue was purified by silica gel column chromatography (n-hexane:ethyl acetate=4:1), obtaining 29.0 g of ethyl S-4-{3-{4-[3-chloro-1-(4-methylphenyl)propoxy]benzoyl}indol-1-yl}butanoate as a yellow oily substance.

MS(m/z):518, 520(MH$^+$); IR(neat) cm$^{-1}$:1732, 1601, 1572; NMR(CDCl$_3$)δ:1.19(t, 3H), 2.10~2.35(m, 8H), 2.42~2.56(m, 1H), 3.55~3.65(m, 1H), 3.74~3.35(m, 1H), 4.09(q, 2H), 4.21(t, 2H), 5.45(dd, 1H), 6.94(d, 2H), 7.16(d, 2H), 7.25~7.41(m, 5H), 7.51(s, 1H), 7.72(d, 2H), 8.33~3.39 (m, 1H)

Step 3:

Ethyl S-4-{3-{4-[3-chloro-1-(4-methylphenyl)propoxy]benzoyl}indol-1-yl}butanoate (29.0 g) obtained in Step 2 was dissolved in N,N-dimethylformamide (300 ml). 1-(2-Methoxyphenyl)piperazine (12.9 g), potassium carbonate (15.5 g), and potassium iodide (37.2 g) were added to the resultant solution and stirred overnight at 60° C. After cooling, water was added to the reaction mixture, followed by extraction with ethyl acetate. The resultant extract was washed with brine and then dried. The solvent was distilled off. The residue was purified by silica gel column chromatography (n-hexane:ethyl acetate=2:1), obtaining 24.9 g of ethyl S-4-{3-{4-(4-methylphenyl)-3-[4-(2-methoxyphenyl) piperazin-1-yl]propoxy}benzoyl}indol-1-yl}butanoate as a light yellow oily substance.

MS(m/z):674(MH$^+$) IR(KBr)cm$^{-1}$:1732, 1599, 1570; NMR(CDCl$_3$)δ:1.20(t, 3H), 1.98~2.36(m, 9H), 2.50~2.72 (m, 6H), 3.05~3.16(br, 4H), 3.86(s, 3H), 4.09(q, 2H), 4.23(t, 2H), 5.33(dd, 1H), 6.84~7.06(m, 6H), 7.25~7.44(m, 4H), 7.52(s, 1H), 7.73(d, 2H), 8.33~8.38(m, 1H), [α]$_D$20.1° (c=1, CHCl$_3$)

Step 4:

Ethyl S-4-{3-{4-{1-(4-Methylphenyl)-3-[4-(2-methoxyphenyl)-piperazin-1-yl]propoxy}benzoyl}indol-1-yl}butanoate (11.0 g) obtained in Step 3 was dissolved in tetrahydrofuran (50 ml). Ethanol (60 ml) and potassium hydroxide (2.75 g) were added to the resultant solution and stirred overnight at room temperature. After removing the solvent, the residue was purified using an HP-20 column, obtaining 9.58 g of potassium S-4-{3-{4-{1-(4-methylphenyl)-3-[4-(2-methoxyphenyl)piperazin-1-yl] propoxy}benzoyl}indol-1-yl}butanoate as amorphous powder.

MS(m/z):684(MH$^+$); IR(KBr)cm$^{-1}$:1597; NMR(DMSO-d$_6$)δ:1.84~2.22(m, 6H), 2.27(s, 3H), 2.44(t, 2H), 2.45~2.55 (br, 4H), 2.90~3.00(br 4H), 3.76(s, 3H), 4.24(t, 2H), 5.47(t, 1H), 6.82~6.95(m, 4H), 7.02(d, 2H), 7.16~7.36(m, 6H), 7.65(d, 1H), 7.71(d, 2H), 7.95(s, 1H), 8.18~8.23(m, 1H)

Example 30

Potassium R-4-{3-{4-{1-(4-methylphenyl)-3-[4-(2-methoxyphenyl)piperazin-1-yl]propyloxy}benzoyl}indol-1-yl}butanoate Step 1:

R-5,5-diphenyl-2-methyl-3,4-propano-1,3,2-oxazaborolidine (885 mg) was dissolved in 1.0M borane-tetrahydrofuran (18 ml) under argon while cooling on ice bath. Subsequently, 4'-methyl-3-chloropropiophenone (5.48 g) in tetrahydrofuran (60 ml) was added dropwise over 30 minutes and stirred for 30 minutes. 1N HCl (10 ml) was added to the reaction mixture and stirred for a while. Then, the solvent was distilled off. 1N HCl was added to the residue, followed by extraction with ethyl acetate. The extract was sequentially washed with saturated sodium bicarbonate solution and brine in this order and then dried. The solvent was distilled off. The residue was recrystallized with n-hexane (30 ml), obtaining 2.76 g of S-(–)-3-chloro-1-(4-methylphenyl)-1-propanol as colorless crystals.

Step 2:

S-(–)-3-chloro-1-(4-methylphenyl)-1-propanol (1.44 g) and ethyl 4-[3-(4-hydroxybenzoyl)indol-1-yl]butanoate (2.74 g) were dissolved in tetrahydrofuran (30 ml). Triphenylphosphine (2.46 g) and diethylazodicarboxylate (1.72 ml) were added to the resultant solution while cooling on ice and stirred for 3 hours at room temperature. After removing the solvent, the residue was purified by silica gel column chromatography (n-hexane:ethyl acetate=4:1), obtaining 2.53 g of ethyl R-4-{3-{4-[3-chloro-1-(4-methylphenyl) propoxy]benzoyl}indol-1-yl}butanoate as a yellow oily substance.

Subsequently, potassium R-4-{3-{4-{1-(4-methylphenyl)-3-[4-(2-methoxyphenyl)piperazin-1-yl] propoxy}benzoyl}indol-1-yl}butanoate was obtained in a manner similar to that described in Steps 3 and 4 of Example 29.

MS(m/z):684(MH$^+$); IR(KBr)cm$^{-1}$:1597; NMR(DMSO$_6$) δ:1.84~2.22(m, 6H), 2.27(s, 3H), 2.44(t, 2H), 2.45~2.55(br, 4H), 2.90~3.00(br 4H), 3.76(s, 3H), 4.24(t, 2H), 5.47(t, 1H), 6.82~6.95(m, 4H), 7.02(d, 2H), 7.16~7.36(m, 6H), 7.65(d, 1H), 7.71(d, 2H), 7.95(s, 1H), 8.18~8.23(m, 1H)

Example 31

Potassium S-4-{3-{3-methoxy-4-{1-(4-methylphenyl)-3-[4-(2-methoxyphenyl)piperazin-1-yl] propoxy}benzoyl}indol-1-yl}butanoate R-(+)-3-chloro-1-(4-methylphenyl)-1-propanol (430 mg) obtained in Step 1 of Example 29 and 1-phenylsulfonyl-3-(3-methoxy-4-hydroxybenzoyl)indole (950 mg) were dissolved in tetrahydrofuran (10 ml). Triphenylphosphine (733 mg) and diethylazodicarboxylate (0.5 ml) were added to the resultant solution and stirred for 1 hour at room temperature. After removing the solvent, the residue was purified by silica gel column chromatography (n-hexane:ethyl acetate=6:1), obtaining 880 mg of S-1-phenylsulfonyl-3-{3-methoxy-4-[3-chloro-1-(4-methylphenyl)propoxy]benzoyl}indole as a yellow oily substance.

MS(m/z):574, 576(MH$^+$); IR(KBr)cm$^{-1}$:1638, 1595, 1580; NMR(CDCl$_3$)δ:2.20~2.37(m, 4H), 2.53~2.67(m, 1H), 3.60~3.70(m, 1H), 3.84~3.98(m, 4H), 5.48(dd, 1H), 6.82(d, 1H), 7.19(d, 2H), 7.30~7.51(m, 8H), 7.53~7.61(m, 1H), 7.87~7.92(m, 2H), 7.97~8.02(m, 2H), 8.18~8.23(m, 1H)

Using the compound obtained in the above-described step in a manner similar to that of Example 1, potassium S-4-{3-{3-methoxy-4-{1-(4-methylphenyl)-3-[4-(2-methoxyphenyl)-piperazin-1-yl]propoxy}benzoyl}indol-1-yl}butanoate was obtained.

MS(m/z):714(MH⁺); IR(KBr)cm⁻¹:1593, 1576; NMR (DMSO-d₆)δ:1.84~2.04(m, 5H), 2.10~2.31(m, 4H), 2.44(t, 2H), 2.45~2.55(br, 4H), 2.92~3.01(br, 4H), 3.76(s, 3H), 3.89(s, 3H), 4.24(t, 2H), 5.46(t, 1H), 6.82~6.96(m, 5H), 7.14~7.38(m, 8H), 7.66(d, 1H), 8.00 (s, 1H), 8.19~8.24 (m, 1H)

Examples 32–36

Similar to Examples 29–31, the compounds of Examples 32 through 36 described below were obtained.

Example 32

Potassium R-4-{3-{3-methoxy-4-{1-(4-methylphenyl)-3-[4-(2-methoxyphenyl)piperazin-1-yl]propoxy}benzoyl}indol-1-yl}butanoate MS(m/z):714(MH⁺); IR(KBr)cm⁻¹:1593, 1572; NMR (DMSO-d₆)δ:1.84~2.04(m, 5H), 2.10~2.31(m, 4H), 2.44(t, 2H), 2.45~2.55(br, 4H), 2.92~3.01(br, 4H), 3.76(s, 3H), 3.89(s, 3H), 4.24(t, 2H), 5.46(t, 1H), 6.82~6.96(m, 5H), 7.14~7.38(m, 8H), 7.66(d, 1H), 8.00(s, 1 H), 8.19~8.24(m, 1H)

Example 33

Potassium R-4-{3-{3-methoxy-4-{1-phenyl-3-[4-(2-methoxyphenyl)piperazin-1-yl]propoxy}benzoyl}indol-1-yl}butanoate MS(m/z):700(MH⁺); IR(KBr)cm⁻¹:1572, 1501; NMR (DMSO-d₆)δ:1.86~2.25(m, 6H), 2.49(t, 2H), 2.50~2.60(br, 4H), 2.91~3.01(br, 4H), 3.76(s, 3H), 3.90(s, 3H), 4.27(t, 2H), 5.51(t, 1H), 6.82~6.98(m, 5H), 7.18~7.48(m, 9H), 7.62(d, 1H), 8.02(s, 1H), 8.18~8.24(m, 1H),

Example 34

Potassium R-4-{3-{3-methoxy-4-{1-phenyl-3-[4-(2-ethoxyphenyl)piperazin-1-yl]propoxy}benzoyl}indol-1-yl}butanoate MS(m/z):714(MH⁺); IR(KBr)cm⁻¹:1595, 1522; NMR (DMSO-d₆)δ:1.83(t, 3H), 1.93~2.26(m, 6H), 2.40~2.60(m, 6H), 2.95~3.05(br 4H), 3.90(s, 3H), 4.00(q, 2H), 4.28(t, 2H), 5.52(t, 1H), 6.84~6.96(m, 5H), 7.20~7.48(m, 9H), 7.58~7.64(m, 1H), 8.03(s, 1H), 8.20~8.24(m, 1H)

Example 35

Potassium S-4-{3-{3-methoxy-4-{1-phenyl-3-[4-(2-methoxyphenyl)piperazin-1-yl]propoxy}benzoyl}indol-1-yl}butanoate MS(m/z):700(MH⁺); IR(KBr)cm⁻¹:1570, 1501; NMR (DMSO-d₆)δ:1.85~2.25(m, 6H), 2.46(t, 2H), 2.49~2.59(br, 4H), 2.89~2.99(br, 4H), 3.76(s, 3H), 3.90(s, 3H), 4.24(t, 2H), 5.51(t, 1H), 6.83~6.97(m, 5H), 7.18~7.47(m, 9H), 7.65(d, 1H), 7.99(s, 1H), 8.19~8.24(m, 1H)

Example 36

Potassium S-4-{3-{3-methoxy-4-{1-phenyl-3-[4-(2-ethoxyphenyl)piperazin-1-yl]propoxy}benzoyl}indol-1-yl}butanoate MS(m/z):714(MH⁺); IR(KBr)cm⁻¹:1593, 1576; NMR (DMSO-d₆)δ:1.32(t, 3H), 1.82~2.27(m, 6H), 2.46(t, 2H), 2.45~2.55(br, 4H), 2.93~3.04(br, 4H), 3.90(s, 3H), 3.99(q, 2H), 4.25(t, 2H), 5.51(t, 1H), 6.80~6.92(m, 4H), 6.95(d, 1H), 7.18~7.49(m, 9H), 7.66(d, 1H), 8.01(s, 1H), 8.20~8.26 (m, 1H)

The structures of the compounds obtained in Examples 29 through 36 are shown in Table 2.

TABLE 2

| Example No. | R1 | R2 (absolute configuration) | R3 | M |
|---|---|---|---|---|
| 29 | Me | 4-Me—Ph(S) | H | K |
| 30 | Me | 4-Me—Ph(R) | H | K |
| 31 | Me | 4-Me—Ph(S) | MeO | K |
| 32 | Me | 4-Me—Ph(R) | MeO | K |
| 33 | Me | Ph(R) | Meo | K |
| 34 | Et | Ph(R) | MeO | K |
| 35 | Me | Ph(S) | MeO | K |
| 36 | Et | Ph(S) | MeO | K |

Example 37

Potassium 4-{3-{4-(4-methylphenylmethoxy)-3-{3-[4-(2-methoxyphenyl)piperazin-1-yl]propoxy}benzoyl}indol-1-yl}butanoate

Method A

Step 1:

3-(3-Chloropropoxy)-4-benzyloxybenzoyl chloride, which was prepared using 4-benzyloxy-3-(3-chloropropoxy)benzoic acid (2.53 g) and oxalyl chloride (1 ml), was dissolved in dichloroethane (20 ml). Aluminum chloride (2.63 g) was added to the resultant solution while cooling on ice bath, stirred for 5 minutes at room temperature, and then cooled again on ice bath. 1-(Phenylsulfonyl)indole (1.69 g) in dichloroethane (10 ml) was added dropwise to the resultant mixture and stirred for 2.5 hours at room temperature. The reaction mixture was poured into 1N HCl and extracted with ethyl acetate. The resultant extract was sequentially washed with saturated sodium bicarbonate solution and brine and then dried. The solvent was distilled off. The residue was purified by silica gel column chromatography (n-hexane:ethyl acetate=3:1), obtaining 0.76 g of 3-[4-hydroxy-3-(3-chloropropoxy) benzoyl]-1-(phenylsulfonyl) indole as a yellow oily substance.

MS(EI, m/z):469, 471(M⁺); IR(KBr)cm⁻¹:1638, 1593; NMR(CDCl₃)δ:2.35(quint, 2H), 3.76(t, 2H), 4.33(t, 2H), 6.03(br, 1H), 7.05(d, 1H), 7.34~7.63(m, 7H), 7.91~8.03(m, 4H), 8.18~8.22(m, 1H)

Step 2:
3-[4-Hydroxy-3-(3-chloropropoxy)benzoyl]-1-(phenylsulfonyl)indole (0.72 g) obtained in Step 1 was dissolved in N,N-dimethylformamide (7 ml). α-bromo-p-xylene (0.37 g) and potassium carbonate (0.28 g) were added to the resultant solution and stirred for 2 hours at room temperature. 2N HCl was added to the reaction mixture, followed by extraction with ethyl acetate. The resultant extract was sequentially washed with saturated sodium bicarbonate solution and brine and then dried. The solvent was distilled off. The residue was purified by silica gel column chromatography (n-hexane:ethyl acetate=3:1), obtaining 0.49 g of 3-[4-(4-methylphenylmethoxy)-3-(3-chloropropoxy)benzoyl]-1-(phenylsulfonyl)indole as a yellow oily substance.

MS(EI, m/z):573, 575(M⁺); IR(KBr)cm⁻¹:1638, 1595; NMR(CDCl₃)δ:2.31(quint, 2H), 2.38(s, 3H), 3.79(t, 2H), 4.25(t, 2H), 5.21(s, 2H), 7.01(d, 1H), 7.20~7.62(m, 11H), 7.89~8.02(m, 4H), 8.20~8.23(m, 1H)

Step 3:
3-[4-(4-Methylphenylmethoxy)-3-(3-chloropropoxy) benzoyl]-1-(phenylsulfonyl)indole (0.44 g) obtained in Step 2 was dissolved in N,N-dimethylformamide (5 ml). 1-(2-Methoxyphenyl)piperazine (0.20 g), potassium carbonate (0.14 g), and potassium iodide (0.38 g) were added to the resultant solution and the mixture was stirred overnight at 60° C. Water was added to the reaction mixture, followed by extraction with ethyl acetate. The resultant extract was washed with brine and then dried. The solvent was distilled off. The residue was purified by silica gel column chromatography (n-hexane:ethyl acetate=1:3), obtaining 0.29 g of 3-{4-(4-methylphenylmethoxy)-3-{3-[4-(2-methoxyphenyl)piperazin-1-yl]propoxy}benzoyl}-1-(phenylsulfonyl)indole (0.29 g) as a light yellow oily substance.

MS(EI, m/z):729(M⁺); IR(KBr)cm⁻¹:1638, 1593; NMR (CDCl₃)δ: 2.07~2.13(m, 2H), 3.37(s, 3H), 2.60~2.72(m, 6H), 3.05~3.13(br, 4H), 3.86(s, 3H), 4.20(t, 2H) 5.22(s, 2H) 6.83~7.02(m, 5H), 7.19~7.62(m, 11H), 7.89~8.02(m, 4H), 8.20~8.23(m, 1H)

Step 4:
3-{4-(4-Methylphenylmethoxy)-3-{3-[4-(2-methoxyphenyl) piperazin-1-yl]propoxy}benzoyl}-1-(phenylsulfonyl)indole (0.26 g) obtained in Step 3 was dissolved in a mixture of methanol (1.5 ml) and tetrahydrofuran (1.5 ml). An aqueous solution of 2N potassium hydroxide (0.5 ml) was added to the resultant solution and stirred overnight at room temperature. After removing the solvent, water was added to the residue, followed by extraction with ethyl acetate. The resultant extract was washed with brine and then dried. The solvent was distilled off. The residue was purified by silica gel column chromatography (ethyl acetate), obtaining 0.14 g of 3-{(4-(4-methylphenylmethoxy)-3-{3-[4-(2-methoxyphenyl) piperazin-1-yl]propoxy}benzoyl}-indole as colorless crystals.

mp: 126°-128° C.; MS(EI, m/z):589(M⁺); IR(KBr)cm⁻¹:1609, 1595; NMR(CDCl₃)δ:1.96~2.08(m, 2H), 2.28(s, 3H), 2.55~2.69(m, 6H), 3.05~3.12(br, 4H), 3.83(s, 3H), 4.08(t, 2H), 5.06(s, 2H), 6.83~7.39(m, 13H), 7.44(d, 1H), 7.61(d, 1H), 8.85~8.38(m, 1H), 10.10(br, 1H)

Step 5:
3-{4-(4-Methylphenylmethoxy)-3-{3-[4-(2-methoxyphenyl) piperazin-1-yl]propoxy}benzoyl}indole (0.12 g) obtained in Step 4 was dissolved in N,N-dimethylformamide (2 ml). 4-Bromoethylbutyrate (52 mg) and potassium carbonate (33 mg) were added to the resultant solution and stirred for 3 hours at 60° C. Water was added to the reaction mixture, followed by extraction with ethyl acetate. The resultant extract was washed with brine and then dried. The solvent was distilled off. The residue was purified by silica gel column chromatography (n-hexane:ethyl acetate=1:1), obtaining 0.11 g of ethyl 4-{3-{4-(4-methylphenylmethoxy)- 3-{3-[4-(2-methoxyphenyl) piperazin-1-yl]propoxy}benzoyl}-indol-1-yl}butanoate as a light brown oily substance.

MS(m/z):704(MH⁺); IR(neat)cm⁻¹:1732, 1620, 1595NMR(CDCl₃)δ:1.21(t, 3H), 2.02~2.26(m, 4H) 2.29~2.36(m, 5H), 2.60~2.71(m, 6H), 3.033~3.12(br, 4H), 3.86(s, 3H), 4.10(q, 2H), 4.19(t, 2H), 4.25(t, 2H), 5.19(s, 2H), 6.84~7.03(m, 5H)7.18~7.43(m, 8H), 7.51(d, 1H), 7.59 (s, 1H), 8.35~8.39(m, 1H)

The product was subjected to hydrolysis in a manner similar to that described in Example 1 or 2, obtaining potassium 4-{3-{4-(4-methylphenylmethoxy)-3-{3-[4-(2-methoxyphenyl)piperazin-1-yl]propoxy}benzoyl}indol-1-yl}butanoate.

MS(m/z):714(MH⁺); IR(KBr)cm⁻¹:1593, 1576 ; NMR (DMSO-d₆)δ:1.84~2.02(m, 6H), 2.31(s, 3H), 2.45~2.55(br, 6H), 2.86~2.95(br, 4H) 3.76(s, 3H), 4.12(t, 2H), 4.27(t, 2H) 5.16(s, 2H), 6.78~6.96(m, 4H), 7.13~7.31(m, 5H), 7.24~7.45(m, 4H), 7.63~7.68(m, 1H), 8.02(s, 1H), 8.21~8.26(m, 1H)

Method B
Step 1:
Ethyl 4-[3-(3,4-dihydroxybenzoyl)indol-1-yl]butanoate (5.70 g) was dissolved in N,N-dimethylformamide (40 ml). α-bromo-p-xylene (3.72 g) and potassium carbonate (2.57 g) were added to the resultant solution and stirred for 3 hours at room temperature. The reaction mixture was poured into 2N HCl and extracted with ethyl acetate. The resultant extract was sequentially washed with saturated sodium bicarbonate solution and brine, and then dried. The solvent was distilled off. The residue was purified by silica gel column chromatography (n-hexane:ethyl acetate=3:1), obtaining 2.77 g of ethyl 4-{3-[3-hydroxy-4-(4-methylphenylmethoxy)benzoyl]indol-1-yl}butanoate (2.77 g) as light brown crystals.

mp: 125°-127° C.
MS (M/z):472(MH⁺); IR(KBr)cm⁻¹:1727, 1617, 1597; NMR(CDCl₃)δ:1.22(t, 3H), 2.14~2.34(m, 4H) 2.39(s, 3H), 4.11(q, 2H), 4.25(t, 2H), 5.15(s, 2H), 5.78(s, 1H), 7.01(d, 1H), 7.21~7.43(m, 8H) 7.47(d, 1H), 7.59(s, 1H) 8.37~8.43 (m, 1H)

Step 2:
Ethyl 4-{3-[3-hydroxy-4-(4-methylphenylmethoxy) benzoyl]indol-1-yl}butanoate (2.77 g) obtained in Step 1 was dissolved in N,N-dimethylformamide (30 ml). 1-Bromo-3-chloropropane (1.39 g) and potassium carbonate (0.97 g) were added to the resultant solution and stirred for 6 hours at 60° C. The reaction mixture was poured into 2N HCl and extracted with ethyl acetate. The resultant extract was sequentially washed with saturated sodium bicarbonate solution and brine and then dried. The solvent was distilled off. The residue was purified by silica gel column chromatography (n-hexane:ethyl acetate=3:1), obtaining 2.67 g of ethyl 4-{3-[4-(4-methylphenylmethoxy)-3-(3-chloropropoxy)benzoyl]indol-1-yl}butanoate as a light yellow oily substance.

MS(m/z):548(MH⁺); IR(neat) cm⁻¹:1730, 1620, 1597; NMR(CDCl₃)δ:1.21(t, 3H), 2.15~2.35(m, 6H) 2.37(s, 3H), 3.77(t, 2H), 4.10(q, 2H), 4.20~4.29(m, 4H), 5.17(s, 2H), 6.97(d, 1H), 7.17~7.45(m, 8H), 7.50 (d, 1H), 7.59(s, 1H), 8.35~8.40 (m, 1H)

Step 3:

Ethyl 4-{3-[4-(4-methylphenylmethoxy)-3-(3-chloropropoxy)benzoyl]indol-1-yl}butanoate (2.59 g) obtained in Step 2 was dissolved in N,N-dimethylformamide (30 ml). 1-(2-Methoxyphenyl)piperazine (1.36 g), potassium carbonate (0.85 g), and potassium iodide (1.02 g) were added to the resultant solution and stirred overnight at 60° C. The reaction mixture was poured into water and extracted with ethyl acetate. The resultant extract was washed with brine and then dried. The solvent was distilled off. The residue was purified by silica gel column chromatography (n-hexane:ethyl acetate=1:2), obtaining 2.47 g of ethyl 4-{3-{4-(4-methylphenylmethoxy)-3-{3-[4-(2-methoxyphenyl)piperazin-1-yl]propoxy}benzoyl}indol-1-yl}butanoate as a colorless oily substance.

The product was subjected to hydrolysis in a manner similar to that described in Example 1 or 2, obtaining potassium 4-{3-{4-(4-methylphenylmethoxy)-3-{3-[4-(2-methoxyphenyl)piperazin-1-yl]propoxy}benzoyl}indol-1-yl}butanoate.

Examples 38–44

Similar to Example 37, the compounds of Examples 38 through 48 described below were prepared.

Example 38

Potassium 4-{3-{4-benzyloxy-3-{3-[4-(2-methoxyphenyl)piperazin-1-yl]propoxy}benzoyl}indol-1-yl}butanoate MS(m/z):700 (MH⁺); IR(KBr)cm⁻¹:1595, 1576; NMR (DMSO-d₆)δ1.86~2.04 (m, 4H), 2.10~2.18 (m, 2H), 2.45~2.55 (m, 6H), 2.86~2.96 (br, 4H) 3.76 (s, 3H), 4.13 (t, 2H), 4.29 (t, 2H) 5.22 (s, 2H), 6.77~6.95 (m, 4H), 7.15~7.52 (m, 10H), 7.60~7.65 (m, 1H), 8.04 (s, 1H), 8.22~8.26 (m, 1H)

Example 39

4-{3-{4-Benzyloxy-3-{1-(4-methylphenyl)-3-[4-(2-methoxyphenyl)piperazin-1-yl]propoxy}benzoyl}indol-1-yl}butanoic acid MS(m/z):752 (MH⁺); IR(KBr)cm⁻¹:1595, 1572; NMR (CDCl₃)δ:2.08~2.45 (m, 8H), 2.75~2.85 (m, 1H), 3.00~3.17 (m, 6H), 3.20~3.36 (br, 4H), 3.86 (s, 3H), 4.31~4.42 (m, 1H), 4.52~4.64 (m, 1H), 5.21 (s, 2H), 5.52~5.60 (m, 2H), 6.85~7.07 (m, 7H), 7.20~7.48 (m, 12H), 7.73 (s, 1H) 8.45~8.52 (m, 1H)

Example 40

Sodium 4-{3-{4-(4-methylphenylmethoxy)-3-{3-[4-(2-propoxyphenyl)piperazin-1-yl]propoxy}benzoyl}indol-1-yl}butanoate MS(m/z):726 (MH⁺); IR(KBr)cm⁻¹:1595, 1576; NMR (DMSO-d₆)δ:1.02 (t, 3H), 1.67~2.00 (m, 8H), 2.31 (s, 3H), 2.45~2.55 (br, 6H), 2.90~3.00 (br, 4H), 3.90 (t, 2H), 4.13 (t, 2H), 4.26 (t, 2H), 5.15 (s, 2H), 6.76~6.92 (m, 4H), 7.12~7.31 (m, 5H), 7.35~7.47 (m, 4H), 7.69 (dd, 1H), 8.00 (s, 1H), 8.20~8.25 (m, 1H)

Example 41

Potassium 4-{3-{4-(4-methylphenylmethoxy)-3-{3-[4-(2-isopropoxyphenyl)piperazin-1-yl]propoxy}benzoyl}indol-1-yl}butanoate MS(m/z):742 (MH⁺); IR(KBr)cm⁻¹:1593, 1574; NMR (DMSO-d₆)δ:1.26 (d, 6H), 1.89~2.06 (m, 4H), 1.99~2.23 (m, 2H), 2.31 (s, 3H), 2.48~2.69 (m, 6H), 2.96~3.03 (m, 4H), 4.11~4.21 (m, 2H), 4.27~4.38 (m, 2H), 4.51~4.62 (m, 1H), 5.17 (s, 2H), 6.83~6.88 (m, 5H), 7.15~7.41 (m, 8H), 7.63 (d, 1H), 8.04 (s, 1H), 8.24 (d, 1H)

Example 42

Potassium 4-{3-{4-(4-fluorophenylmethoxy)-3-{3-[4-(2-methoxyphenyl)piperazin-1-yl]propoxy}benzoyl}indol-1-yl}butanoate MS(m/z):718 (MH⁺); IR(KBr)cm⁻¹:1595, 1575; NMR (DMSO-d₆)δ:1.85~2.20 (m, 6H), 2.40~2.55 (m, 6H), 2.85~2.96 (br, 4H), 3.76 (s, 3H), 4.13 (t, 2H), 4.29 (t, 2H), 5.20 (s, 2H), 6.77~6.95 (m, 4H), 7.15~7.33 (m, 5H), 7.38~7.45 (m, 2H), 7.50~7.65 (m, 3H), 8.03 (s, 1H), 8.20~8.26 (m, 1H)

Example 43

Sodium 4-{3-{4-(4-ethylphenylmethoxy)-3-{3-[4-(2-methoxyphenyl)piperazin-1-yl]propoxy}benzoyl}indol-1-yl}butanoate MS(m/z):711 (MH⁺); IR(KBr)cm⁻¹:1593, 1572; NMR (DMSO-d₆)δ:1.17 (t, 3H), 1.79~1.98 (m, 6H), 2.45~2.55 (br, 6H), 2.61 (q, 2H), 2.87~2.97 (br, 4H), 3.76 (s, 3H), 4.13 (t, 2H), 4.27 (t, 2 H), 5.17 (s, 2H), 6.76~6.96 (m, 4H), 7.15~7.30 (m, 5H), 7.38~7.46 (m, 4H), 7.66~7.72 (m, 1H), 8.01 (s, 1H), 8.20~8.25 (m, 1H)

Example 44

Potassium 4-{3-{4-(4-phenylbutoxy)-3-{3-[4-(2-methoxyphenyl)piperazin-1-yl]propoxy}benzoyl}indol-1-yl}butanoate MS(m/z):742 (MH⁺); IR(KBr)cm⁻¹:1595, 1573; NMR (DMSO-d₆)δ:1.72~1.99 (m, 10H), 2.42~2.53 (m, 6H), 2.68 (t, 2H), 2.86~2.95 (br, 4 H), 3.76 (s, 3H), 4.04~4.13 (m, 4H), 4.27 (t, 2H), 6.78~6.96 (m, 4H), 7.07 (d, 1H), 7.13~7.31 (m, 7H), 7.37 (d, 1H), 7.45 (dd, 1H), 7.67 (dd, 1H), 8.00 (s, 1H), 8.20~8.25 (m, 1H)

Example 45

Potassium 4-{3-{4-(4-methylphenylmethoxy)-3-{3-[4-(2-ethoxyphenyl)piperazin-1-yl]propoxy}benzoyl}indol-1-yl }butanoate MS(m/z):728 (MH⁺); IR(KBr)cm⁻¹:1593, 1575; NMR (DMSO-d₆)δ:1.33 (t, 3H), 1.92~1.99 (m, 4H), 2.05~2.09 (m, 2H), 2.31 (s, 3H) 2.49~2.51 (m, 6H), 2.90~2.98 (m, 4H), 4.00 (q, 2H), 4.12 (t, 2H), 4.28 (t, 2H), 5.16 (s, 2H), 6.77~6.90 (m, 4H), 7.14~7.31 (m, 5H), 7.36~7.44 (m, 4H), 7.64 (d, 1H), 8.02 (s, 1H), 8.23 (dd, 1H)

Example 46

Potassium 4-{3-{3-{4-[4-(2-methoxyphenyl)piperazin-1-yl]butoxy}-4-(4-methylphenylmethoxy)benzoyl}indol-1-yl}butanoate MS(m/z):728 (MH$^+$); IR(KBr)cm$^{-1}$:1593, 1576; NMR (DMSO-d$_6$)δ:1.59~1.64 (m, 2H), 1.75~1.82 (m, 2H), 1.89~1.96 (m, 4H), 2.30 (s, 3H), 2.37 (t, 2H), 2.47~2.53 (m, 4H), 2.88~2.94 (m 4H), 3.76 (s, 3H), 4.10 (t, 2H), 4.24~4.28 (m, 2H) 5.15 (s, 2H), 6.82~6.93 (m, 4H) 7.15~7.30 (m, 5H), 7.36~7.4 (m, 4H), 7.67 (d, 1H), 8.01 (s, 1H) 8.22 (dd, 1H)

Example 47

Potassium 4-{3-{3-{4-[4-(2-ethoxyphenyl)piperazin-1-yl]butoxy}-4-(4-methylphenylmethoxy)benzoyl}indol-1-yl}butanoate MS(m/z):742(MH$^+$); IR(KBr)cm$^{-1}$:1593, 1575; NMR (DMSO-d$_6$)δ:1.32~2.01 (t, 3 H), 1.57~1.69 (m, 2H), 1.64~2.12 (m, 6 H), 2.18 (t, 2H), 2.29 (s, 3 H), 2.38 (t, 2 H), 2.48~2.50 (m, 4H), 2.87~2.98 (m, 4 H), 3.99 (q, 2 H), 4.10 (t, 2 H), 4.29 (t,2H), 5.16 (s, 2 H),6.80~6.89 (m, 4 H), 7.15~7.42 (m, 9H), 7.63 (d, 1 H), 8.03 (s, 1 H), 8.23 (dd, 1 H),

Example 48

Potassium 4-{3-{3-{2-[4-(2-methoxyphenyl)piperazin-1-yl]ethoxy}-4-(4-methylphenylmethoxy)benzoyl}indol-1-yl}butanoate MS(m/z):700(MH+); IR(KBr)cm$^{-1}$:1593, 1574; NMR (DMSO-d$_6$)δ:1.93~2.01 (m, 2 H), 2.02~2.10 (m, 2 H), 2.30 (s, 3 H), 2.62~2.70 (m, 2 H), 2.74~2.81 (m, 2 H), 2.86~2.94 (m, 4 H), 3.76(s, 3 H), 4.21 (t, 2 H), 4.29 (t, 2 H), 5.16 (s,2H), 6.82~6.93 (m, 4 H) 7.1 6~7.32 (m, 5 H), 7.37~7.44 (m, 4 H), 7.66 (d, 1 H), 8.04 (s, 1 H), 8.22 (dd, 1 H), The structures of the compounds obtained in Examples 37 through 48 are shown in Table 3.

95% $O_2$ and 5% $CO_2$. The isometric contraction under a resting tension of 1 g was recorded with a force-displacement transducer(TB-651T, Nihon Koden) on a recoder(RECTI HORIZ 8K, Nihon Sanei).

After an equilibration of tissues at least 60 minutes, contractions were elicited by repeated dose of phenylephrine until constant contraction responses were obtained. Subsequently, the dose-response curves were obtained by increasing concentrations of phenylephrine($10^{-7}$–×$10^{-4}$M). After the resting period for 60 minutes, tissues were incubated with test drugs for 30 minutes and dose-response curves were constructed as described above.

In all cases, $10^{-5}$M propranolol(β-adrenoceptor antagonist) was administered 10 minutes before the contraction by phenylephrine.

The composition of the Krebs-Henseleit solution was as follows(mM): NaCl 118.4, KCl 4.7, MgSO$_4$ 1.2, CaCl$_2$ 2.5, NaHCO$_3$ 25.0, glucose 11.1, KH$_2$PO$_4$ 1.2.

The potency of each test drug was expressed as the pA$_2$ value(negative logarithm of the antagonist dissociation constant). The results are shown in Table 4.

TABLE 4

| α$_1$-Adrenoceptor blocking action | | |
|---|---|---|
| Example No. | Urethra (pA$_2$) | Prostate (pA$_2$) |
| 1 | 6.42 | 7.06 |
| 3 | 6.94 | 7.12 |
| 5 | 5.96 | 6.85 |

TABLE 3

Structure: 2-OR$^1$-phenyl–N(piperazine)N–(CH$_2$)$_n$–CH(R$^2$)–O–[phenyl with R$^3$]–C(=O)–[indol-3-yl with N-CH$_2$CH$_2$CH$_2$COOM]

| Example No. | R1 | R2 | R3 | n | M |
|---|---|---|---|---|---|
| 37 | Me | H | 4-Me—PhCH$_2$O | 2 | K |
| 38 | Me | H | PhCH$_2$O | 2 | K |
| 39 | Me | 4-Me—Ph | PhCH$_2$O | 2 | H |
| 40 | n-Pr | H | 4-Me—PhCH$_2$O | 2 | Na |
| 41 | i-Pr | H | 4-Me—PhCH$_2$O | 2 | K |
| 42 | Me | H | 4-F——PhCH$_2$O | 2 | K |
| 43 | Me | H | 4-Et—PhCH$_2$O | 2 | Na |
| 44 | Me | H | 4-Ph(CH$_2$)$_4$O | 2 | K |
| 45 | Et | H | 4-Me—PhCH$_2$O | 2 | K |
| 46 | Me | H | 4-Me—PhCH$_2$O | 3 | K |
| 47 | Et | H | 4-Me—PhCH$_2$O | 3 | K |
| 48 | Me | H | 4-Me—PhCH$_2$O | 1 | K |

Test Example 1

α$_1$-Adrenoceptor Blocking Action

Male albino rabbits were sacrificed by exsanguination, and the prostate and urethra were isolated. After removal of fat and connective tissues, transverse smooth muscle strips were prepared from prostate and proximal urethra. Each segmental strip was suspended in an organ bath at 37° C. in a Krebs-Henseleit solution which had been bubbled with

TABLE 4-continued

| α$_1$-Adrenoceptor blocking action | | |
|---|---|---|
| Example No. | Urethra (pA$_2$) | Prostate (pA$_2$) |
| 14 | 6.41 | 7.14 |
| 15 | 6.60 | 7.30 |

TABLE 4-continued

| $\alpha_1$-Adrenoceptor blocking action | | |
|---|---|---|
| Example No. | Urethra (pA$_2$) | Prostate (pA$_2$) |
| 16 | 6.81 | 7.07 |
| 20 | 6.16 | 6.25 |
| 24 | 6.20 | 7.00 |
| 28 | 6.78 | 6.99 |
| 35 | 7.19 | 7.56 |
| 37 | 6.92 | 7.72 |
| 38 | 7.44 | 7.78 |
| 42 | 6.40 | 7.15 |
| 45 | 7.25 | 7.46 |

Test Example 2
Testosterone 5α-Reductase Inhibitory Action

Male Wistar rats (age: 9–10 weeks old) were anesthetized with ethyl ether and ventral prostates were dissected. The isolated prostates were weighed and homogenized with ultradisperser(Yamato, Japan) and teflon-glass homogenizer in 3 tissue volumes of 50 mM Tris-HCl buffer(pH 7.2) containing 0.25M sucrose and 1 mM dithiothreitol. The homogenates were filtered with gauze and centrifuged at 3,000 rpm for 10 minutes at 4° C. The pellets were resuspended in same buffer as described above and the resultant suspension was used as the nuclear fraction.

Testosterone 5α-reductase activity was carried out described as follows. The reaction mixture contained 0.ml of nuclear fraction 0.1 ml of 5 mM NADPH, 0.01 ml of test drug dissolved in dimethylsulfoxide and 0.78ml of Tris-HCl buffer(pH 7.0). The reaction was started by addition of 0.01 ml of 150 µM [4-$^{14}$C]-testosterone and incubated for 60 minutes at 37° C. After incubation, reaction was stopped by adding 4 ml of ethyl acetate. 3 ml of ethyl acetate was evaporated under nitrogen to dryness and dissolved in 40 µl of ethyl acetate. 10 µl of ethyl acetate was applied to silica gel thin layer plate(HF$_{254}$, Merck) and the plate was developed in ethyl acetate and cyclohexane(1:1). The plate was subjected to autoradiography and the radioactivity profiles were determined by scraping the spots of testosterone, dihydrotestosterone and other metabolites and counting in a scintillation counter. Testosterone 5a -reductase activity was calculated for the total radioactivity and radioactivities of dihydrotestosterone and other metabolites. The inhibitory activity of test drug was expressed as IC$_{50}$(nM). The results are shown in Table 5.

TABLE 5

| Testosterone 5α-reductase inhibitory action | |
|---|---|
| Example No. | IC$_{50}$ (nM) |
| 1 | 3.7 |
| 8 | 0.26 |
| 11 | 3.1 |
| 13 | 1.4 |
| 15 | 7.9 |
| 22 | 3.7 |
| 26 | 5.0 |
| 35 | 6.8 |
| 37 | 3.5 |
| 45 | 1.5 |
| 46 | 1.5 |

From Tables 5 and 6, it is apparent that the compound (1) of the present invention or a salt thereof has excellent $\alpha_1$-adrenergic receptor blocking action and testosterone 5α-reductase inhibitory action.

Test Example 3

Toxicity Test:

Groups of ICR mice (Charles River, age: 4–5 weeks old), each group consisting of 10 mice, were used. A compound of each Example was suspended in 10% gum arabic. The suspension was intraperitoneally administered to each mouse at a dose of 100 mg/kg. The mice were observed over 7 days. No casualty took place at this dosage.

Preparation Example 1

The compound (20 g) of Example 1, lactose (315 g), corn starch (125 g), and crystalline cellulose (25 g) were mixed uniformly. An aqueous 7.5% solution (200 ml) of hydroxypropylcellulose was added thereto. The resultant mixture was granulated with an extruding granulator equipped with a screen having a mesh of 0.5 mm diameter. The thus-prepared granules were immediately rounded with a marumerizer and then dried, obtaining a granular agent.

Preparation Example 2

Granules prepared in Preparation Example 1 were coated with a film coating liquid (1.9 kg) having the following composition using a fluidized granulator, thereby obtaining an enteric granular agent.

Composition of coating liquid: hydroxypropylmethylcellulose phthalate (5.0%), stearic acid (0.25%), methylene chloride (50.0%), ethanol (44.75%)

Preparation Example 3

The compound (20 g) of Example 15, lactose (100 g), corn starch (36 g), crystalline cellulose (30 g), carboxymethylcellulose calcium (10 g), and magnesium stearate (4 g) were mixed uniformly. The resultant mixture was formed into tablets, 200 mg each, using a single-punch tableting machine which has a pestle of 7.5 mm in diameter.

Preparation Example 4

Tablets prepared in Preparation Example 3 were spray-coated with a coating liquid having the following composition, thereby obtaining enteric film-coated tablets, each coated with 10 mg coating.

Composition of coating liquid: hydroxypropylmethylcellulose phthalate (8.0%), maibaset (0.4%), methylene chloride (50.0%), bleached beeswax (0.1%), and isopropanol (41.5%)

Preparation Example 5

The compound (200 g) of Example 22, polysorbate 80 (20 g), and medium chain fatty acid triglyceride (1780 g) were mixed and dissolved completely. Subsequently, the resultant solution was formed into a soft capsulated agent, each capsule containing 200 mg of the solution, by a rotary method using a soft capsulating liquid, which is composed of gelatin (100 parts), thick glycerin (30 parts), ethyl paraben (0.4 parts), and propyl paraben (0.2 parts).

Preparation Example 6

| Compound of Example 23 | | 100 mg |
|---|---|---|
| Sodium acetate | | 2 mg |
| Acetic acid (for preparation to pH 5.8) | | Suitable amount |
| Distilled water | | Balance |
| | Total | 10 ml/vial |

The above ingredients were processed by a routine method to obtain an injection agent.

Industrial Applicability

The compound (1) of the present invention has both $\alpha_1$-adrenergic receptor blocking action and testosterone 5α-reductase inhibitory action, and thus is useful as a remedy and/or a preventive for diseases caused by overproduction of dihydrotestosterone, e.g., prostatic hypertrophy or accompanying urination disorder, male pattern alopecia, and acne.

We claim:

1. An indole derivative represented by the following formula (1) or a salt thereof:

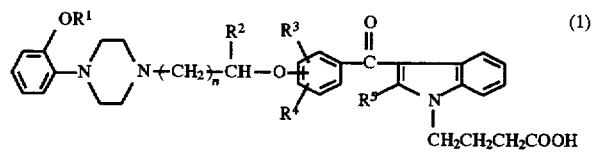

wherein $R^1$ represents lower alkyl; $R^2$ represents hydrogen or phenyl which may be substituted by at least one lower alkyl, lower alkoxy or a halogen atom; $R^3$ represents hydrogen, lower alkyl, lower alkoxy, or phenylalkyloxy which may be substituted by halogen or lower alkyl; $R^4$ represents hydrogen, lower alkyl or lower alkoxy; $R^5$ represents hydrogen or lower alkyl; and n represents an integer of 1 to 5.

2. An indole derivative or a salt thereof as defined in claim 1, wherein the lower alkyl is C1–C6 linear or branched alkyl; and the lower alkoxy is C1–C6 linear or branched alkoxy.

3. An indole derivative or a salt thereof as defined in claim 1, wherein $R^2$ is phenyl which may be substituted by at least one lower alkyl, lower alkoxy, or a halogen atom.

4. An indole derivative or a salt thereof as defined in claim 3, wherein the absolute configuration is an S-configuration.

5. A testosterone 5α-reductase inhibitor comprising as an effective ingredient an indole derivative or a salt thereof as defined in claim 1.

6. An $a_1$-adrenergic receptor blocker comprising as an effective ingredient an indole derivative or a salt thereof as defined in claim 1.

7. A therapeutic agent for prostatic hypertrophy as well as for urination disorder, alopecia, and acne which accompany prostatic hypertrophy, comprising as an effective ingredient an indole derivative or a salt thereof as defined in claim 1.

8. A pharmaceutical composition comprising an indole derivative or a salt thereof as defined in claim 1 and a carrier for pharmaceuticals.

9. A composition as defined in claim 8, which is used for the treatment of prostatic hypertrophy as well as urination disorder, alopecia, and acne which accompany prostatic hypertrophy.

10. A method for the treatment of prostatic hypertrophy as well as urination disorder, alopecia, and acne which accompany prostatic hypertrophy, characterized by administering an effective amount of an indole derivative or a salt thereof as described in claim 1.

* * * * *